US012420101B2

(12) United States Patent
Isaacson et al.

(10) Patent No.: US 12,420,101 B2
(45) Date of Patent: Sep. 23, 2025

(54) MULTIPOLE MAGNET FOR MEDICAL IMPLANT SYSTEM

(71) Applicant: Cochlear Limited, Macquarie University (AU)

(72) Inventors: Nathan Isaacson, Macquarie University (AU); Anthony Powell, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 478 days.

(21) Appl. No.: 17/753,165

(22) PCT Filed: Sep. 23, 2020

(86) PCT No.: PCT/IB2020/058898
§ 371 (c)(1),
(2) Date: Feb. 22, 2022

(87) PCT Pub. No.: WO2021/059163
PCT Pub. Date: Apr. 1, 2021

(65) Prior Publication Data
US 2022/0331598 A1   Oct. 20, 2022

Related U.S. Application Data

(60) Provisional application No. 62/907,044, filed on Sep. 27, 2019.

(51) Int. Cl.
*A61N 1/372*   (2006.01)
*A61N 1/05*   (2006.01)

(52) U.S. Cl.
CPC ....... *A61N 1/37223* (2013.01); *A61N 1/0541* (2013.01)

(58) Field of Classification Search
CPC .............. A61N 1/37223; A61N 1/0541; A61N 1/36038; A61N 1/375
See application file for complete search history.

(56) References Cited

U.S. PATENT DOCUMENTS 3,043,000 A   7/1962   Hatfield
3,487,403 A   12/1969   Pihl
(Continued)

FOREIGN PATENT DOCUMENTS

AU   2009101370 A4   3/2013
CN   2411869 Y   12/2000
(Continued)

OTHER PUBLICATIONS

International Search Report and Written Opinion for PCT/IB2020/058898, 14 pages, dated Dec. 28, 2020.
(Continued)

*Primary Examiner* — John R Downey
(74) *Attorney, Agent, or Firm* — Pilloff Passino & Cosenza LLP; Martin J. Cosenza

(57) ABSTRACT

An apparatus includes a housing configured to be placed over a portion of skin of a recipient, the portion of skin overlaying an implanted device. The apparatus further includes circuitry within the housing. The circuitry is configured to wirelessly communicate with the implanted device. The apparatus further includes a unitary magnet in mechanical communication with the housing. The magnet includes at least one first magnetic dipole moment having a first magnitude and a first direction and at least one second magnetic dipole moment having a second magnitude substantially equal to the first magnitude and a second direction substantially opposite to the first direction.

54 Claims, 8 Drawing Sheets

(56) References Cited

U.S. PATENT DOCUMENTS

| | | |
|---|---|---|
| 3,573,812 A | 4/1971 | Pihl |
| D227,118 S | 6/1973 | Muraoka |
| 3,771,685 A | 11/1973 | Micallef |
| 3,801,767 A | 4/1974 | Marks |
| 3,987,967 A | 10/1976 | Kuznetsov et al. |
| 4,003,521 A | 1/1977 | Hess |
| 4,038,990 A | 8/1977 | Thompson |
| 4,197,840 A | 4/1980 | Beck et al. |
| 4,199,741 A | 4/1980 | Paulet |
| 4,226,164 A | 10/1980 | Carter |
| 4,240,428 A | 12/1980 | Akhavi |
| 4,257,936 A | 3/1981 | Matsumoto et al. |
| 4,317,969 A | 3/1982 | Riegler et al. |
| 4,352,960 A | 10/1982 | Dorner et al. |
| D267,541 S | 1/1983 | Kanemitsu |
| 4,414,701 A | 11/1983 | Johnson |
| 4,596,971 A | 6/1986 | Hirabayashi et al. |
| 4,606,329 A | 8/1986 | Hough |
| 4,610,621 A | 9/1986 | Taber et al. |
| 4,628,907 A | 12/1986 | Epley |
| 4,634,191 A | 1/1987 | Studer |
| 4,676,772 A | 6/1987 | Hooven |
| 4,726,378 A | 2/1988 | Kaplan |
| 4,731,718 A | 3/1988 | Sheu |
| 4,736,747 A | 4/1988 | Drake |
| 4,743,264 A | 5/1988 | Sherva-Parker |
| 4,792,368 A | 12/1988 | Sagawa et al. |
| 4,817,607 A | 4/1989 | Tatge |
| RE32,947 E | 6/1989 | Dormer et al. |
| 4,868,530 A | 9/1989 | Ahs |
| 4,917,504 A | 4/1990 | Scott et al. |
| 4,918,745 A | 4/1990 | Hutchison |
| 4,920,679 A | 5/1990 | Sarles et al. |
| 5,014,592 A | 5/1991 | Zweig et al. |
| 5,015,224 A | 5/1991 | Maniglia |
| 5,096,763 A | 3/1992 | Ogata et al. |
| 5,105,811 A | 4/1992 | Kuzma |
| 5,183,056 A | 2/1993 | Dalen et al. |
| 5,196,710 A | 3/1993 | Kalfaian |
| 5,282,858 A | 2/1994 | Bisch et al. |
| 5,314,453 A | 5/1994 | Jeutter |
| D348,067 S | 6/1994 | Lucey et al. |
| 5,338,287 A | 8/1994 | Miller et al. |
| 5,360,388 A | 11/1994 | Spindel et al. |
| 5,423,317 A | 6/1995 | Iijima et al. |
| 5,456,654 A | 10/1995 | Ball |
| 5,554,096 A | 9/1996 | Ball |
| 5,603,726 A | 2/1997 | Schulman et al. |
| 5,624,376 A | 4/1997 | Ball et al. |
| 5,630,835 A | 5/1997 | Brownlee |
| 5,716,407 A | 2/1998 | Knapp et al. |
| 5,746,897 A | 5/1998 | Heimanson et al. |
| 5,749,912 A | 5/1998 | Zhang et al. |
| 5,757,183 A | 5/1998 | Smith et al. |
| 5,775,652 A | 7/1998 | Crawshaw et al. |
| 5,785,477 A | 7/1998 | McGuffey et al. |
| 5,800,336 A | 9/1998 | Ball et al. |
| 5,857,958 A | 1/1999 | Ball et al. |
| 5,877,664 A | 3/1999 | Jackson, Jr. |
| 5,897,486 A | 4/1999 | Ball et al. |
| 5,913,815 A | 6/1999 | Ball et al. |
| 5,945,762 A | 8/1999 | Chen et al. |
| 5,965,282 A | 10/1999 | Baermann |
| 5,971,334 A | 10/1999 | Crawshaw et al. |
| 6,040,762 A | 3/2000 | Tompkins |
| 6,073,973 A | 6/2000 | Boscaljon et al. |
| 6,101,417 A | 8/2000 | Vogel et al. |
| 6,138,681 A | 10/2000 | Chen et al. |
| 6,157,278 A | 12/2000 | Katznelson et al. |
| 6,157,281 A | 12/2000 | Katznelson et al. |
| 6,175,767 B1 | 1/2001 | Doyle, Sr. |
| 6,178,079 B1 | 1/2001 | Renger |
| 6,178,353 B1 | 1/2001 | Griffith et al. |
| 6,190,305 B1 | 2/2001 | Ball et al. |
| 6,208,235 B1 | 3/2001 | Trontelj |
| 6,208,882 B1 | 3/2001 | Lenarz et al. |
| 6,217,508 B1 | 4/2001 | Ball et al. |
| 6,219,580 B1 | 4/2001 | Faltys et al. |
| 6,244,142 B1 | 6/2001 | Swanson |
| 6,259,951 B1 | 7/2001 | Kuzma et al. |
| 6,263,230 B1 | 7/2001 | Haynor et al. |
| 6,272,382 B1 | 8/2001 | Faltys et al. |
| 6,292,678 B1 | 9/2001 | Hall et al. |
| 6,295,472 B1 | 9/2001 | Rubinstein et al. |
| 6,295,473 B1 | 9/2001 | Rosar |
| 6,308,101 B1 | 10/2001 | Faltys et al. |
| 6,313,551 B1 | 11/2001 | Hazelton |
| 6,348,070 B1 | 2/2002 | Teissl et al. |
| 6,355,998 B1 | 3/2002 | Schöb et al. |
| 6,358,281 B1 | 3/2002 | Berrang et al. |
| 6,401,723 B1 | 6/2002 | Garibaldi et al. |
| 6,475,134 B1 | 11/2002 | Ball et al. |
| 6,505,062 B1 | 1/2003 | Ritter et al. |
| 6,506,987 B1 | 1/2003 | Woods |
| 6,522,909 B1 | 2/2003 | Garibaldi et al. |
| 6,542,777 B1 | 4/2003 | Griffith et al. |
| 6,571,676 B1 | 6/2003 | Folsom et al. |
| 6,643,378 B2 | 11/2003 | Schumaier |
| 6,668,065 B2 | 12/2003 | Lee et al. |
| 6,838,963 B2 | 1/2005 | Zimmerling et al. |
| 6,857,612 B2 | 2/2005 | Goodbred |
| D512,416 S | 12/2005 | Malaver |
| 6,991,594 B2 | 1/2006 | Holcomb |
| 7,038,565 B1 | 5/2006 | Chell |
| 7,091,806 B2 | 8/2006 | Zimmerling et al. |
| 7,190,247 B2 | 3/2007 | Zimmerling |
| 7,191,007 B2 | 3/2007 | Desai et al. |
| 7,200,504 B1 | 4/2007 | Fister |
| 7,225,028 B2 | 5/2007 | Della Santina et al. |
| 7,231,252 B2 | 6/2007 | Duncan et al. |
| 7,266,208 B2 | 9/2007 | Charvin et al. |
| 7,338,028 B2 | 3/2008 | Zimmerling et al. |
| 7,386,143 B2 | 6/2008 | Easter et al. |
| 7,532,937 B2 | 5/2009 | Horio et al. |
| 7,566,296 B2 | 7/2009 | Zimmerling et al. |
| 7,610,096 B2 | 10/2009 | McDonald, III |
| 7,642,887 B2 | 1/2010 | Zimmerling |
| 7,647,120 B2 | 1/2010 | Della Santina et al. |
| 7,695,427 B2 | 4/2010 | Kugler et al. |
| 7,762,998 B2 | 7/2010 | Birk et al. |
| 7,808,348 B2 | 10/2010 | Fullerton et al. |
| 7,856,986 B2 | 12/2010 | Darley |
| 7,976,453 B2 | 7/2011 | Zimmerling et al. |
| 7,991,477 B2 | 8/2011 | McDonald, III |
| 8,013,699 B2 | 9/2011 | Zimmerling |
| 8,118,725 B2 | 2/2012 | Zimmerling et al. |
| 8,211,174 B2 | 7/2012 | Park et al. |
| 8,246,533 B2 | 8/2012 | Chang et al. |
| 8,255,058 B2 | 8/2012 | Gibson et al. |
| 8,260,435 B2 | 9/2012 | Johnson et al. |
| 8,270,647 B2 | 9/2012 | Crawford et al. |
| 8,340,774 B2 | 12/2012 | Hochmair et al. |
| 8,400,038 B2 | 3/2013 | Smith et al. |
| 8,406,443 B2 | 3/2013 | Westerkull et al. |
| 8,515,112 B2 | 8/2013 | Crawford et al. |
| 8,515,544 B2 | 8/2013 | Daly et al. |
| 8,532,783 B2 | 9/2013 | Zimmerling et al. |
| 8,634,909 B2 | 1/2014 | Zimmerling et al. |
| 8,734,475 B2 | 5/2014 | Ekvall et al. |
| 8,744,106 B2 | 6/2014 | Ball |
| 8,758,394 B2 | 6/2014 | Zimmerling et al. |
| 8,768,480 B2 | 7/2014 | Charvin |
| 8,811,643 B2 | 8/2014 | Crawford et al. |
| 8,829,462 B2 | 9/2014 | Clarke et al. |
| 8,829,752 B2 | 9/2014 | Chen et al. |
| 8,897,475 B2 | 11/2014 | Ball et al. |
| 8,983,102 B2 | 3/2015 | Crawford et al. |
| 8,987,951 B2 | 3/2015 | Park |
| 9,002,469 B2 | 4/2015 | D'Ambrosio |
| 9,014,782 B2 | 4/2015 | Miyoshi |
| 9,022,917 B2 | 5/2015 | Kasic et al. |
| 9,042,995 B2 | 5/2015 | Dinsmoor et al. |
| 9,058,962 B2 | 6/2015 | Endo et al. |
| 9,113,268 B2 | 8/2015 | Ball et al. |

(56) References Cited

U.S. PATENT DOCUMENTS

| | | |
|---|---|---|
| RE45,701 E | 9/2015 | Zimmerling et al. |
| 9,136,728 B2 | 9/2015 | Dinsmoor et al. |
| 9,144,676 B2 | 9/2015 | Gibson et al. |
| 9,179,228 B2 | 11/2015 | Ruppersberg et al. |
| 9,210,521 B2 | 12/2015 | Kasic et al. |
| 9,258,656 B2 | 2/2016 | Ruppersberg et al. |
| 9,392,384 B2 | 7/2016 | Crawford et al. |
| 9,420,388 B2 | 8/2016 | Ball |
| 9,526,810 B2 | 12/2016 | Ruppersberg |
| 9,627,120 B2 | 4/2017 | Scott et al. |
| 9,736,601 B2 | 8/2017 | Kasic et al. |
| 9,739,842 B2 | 8/2017 | Holm et al. |
| 9,788,125 B2 | 10/2017 | Ruppersberg et al. |
| RE46,624 E | 12/2017 | Zimmerling et al. |
| 9,872,115 B2 | 1/2018 | Kennes |
| 9,872,993 B2 | 1/2018 | Zimmerling |
| 10,130,807 B2 | 11/2018 | Leigh et al. |
| 10,186,360 B2 | 1/2019 | Shimbo et al. |
| 10,405,891 B2 | 9/2019 | Pool et al. |
| 10,646,712 B2 | 5/2020 | Smith et al. |
| 10,646,718 B2 | 5/2020 | Smith et al. |
| 10,917,730 B2 | 2/2021 | Kennes et al. |
| 10,942,042 B2 | 3/2021 | Bidaux et al. |
| 11,012,796 B2 | 5/2021 | Andersson et al. |
| 11,097,095 B2 | 8/2021 | Smith et al. |
| 2001/0021805 A1 | 9/2001 | Blume et al. |
| 2002/0076071 A1 | 6/2002 | Single |
| 2002/0103430 A1 | 8/2002 | Hastings |
| 2002/0116033 A1 | 8/2002 | Greatbatch et al. |
| 2002/0116034 A1 | 8/2002 | Miller et al. |
| 2002/0120332 A1 | 8/2002 | Law et al. |
| 2003/0034039 A1 | 2/2003 | Schmid et al. |
| 2003/0034705 A1 | 2/2003 | Hakansson |
| 2003/0089933 A1 | 5/2003 | Janesky et al. |
| 2003/0120202 A1 | 6/2003 | Gordon |
| 2003/0139782 A1 | 7/2003 | Duncan |
| 2003/0161481 A1 | 8/2003 | Miller et al. |
| 2003/0161482 A1 | 8/2003 | Miller et al. |
| 2003/0163021 A1 | 8/2003 | Miller et al. |
| 2003/0163022 A1 | 8/2003 | Miller et al. |
| 2003/0171787 A1 | 9/2003 | Money et al. |
| 2003/0171792 A1 | 9/2003 | Zarinetchi et al. |
| 2003/0181956 A1 | 9/2003 | Duncan et al. |
| 2004/0012470 A1 | 1/2004 | Zimmerling et al. |
| 2004/0032962 A1 | 2/2004 | Westerkull |
| 2004/0059423 A1 | 3/2004 | Barnes et al. |
| 2004/0136558 A1 | 7/2004 | Usuki et al. |
| 2004/0147804 A1 | 7/2004 | Schneider et al. |
| 2004/0148025 A1 | 7/2004 | Schneider et al. |
| 2004/0260361 A1 | 12/2004 | Gibson |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2005/0070346 A1 | 3/2005 | Pan |
| 2005/0101830 A1 | 5/2005 | Easter et al. |
| 2005/0159791 A1 | 7/2005 | Daly et al. |
| 2005/0165471 A1 | 7/2005 | Wang et al. |
| 2005/0171579 A1 | 8/2005 | Tasche et al. |
| 2005/0197715 A1 | 9/2005 | Kugler et al. |
| 2005/0216075 A1 | 9/2005 | Wang et al. |
| 2005/0228214 A1 | 10/2005 | Schneider et al. |
| 2005/0228215 A1 | 10/2005 | Schneider et al. |
| 2005/0240098 A1 | 10/2005 | Zhong et al. |
| 2006/0030905 A1 | 2/2006 | Malaver |
| 2006/0045298 A1 | 3/2006 | Westerkull |
| 2006/0056649 A1 | 3/2006 | Schumaier |
| 2006/0084857 A1 | 4/2006 | Massengill et al. |
| 2006/0119356 A1 | 6/2006 | Rabe et al. |
| 2006/0184212 A1 | 8/2006 | Faltys et al. |
| 2006/0217792 A1 | 9/2006 | Hussein et al. |
| 2006/0241746 A1 | 10/2006 | Shaoulian et al. |
| 2006/0244560 A1 | 11/2006 | Zimmerling et al. |
| 2006/0247488 A1 | 11/2006 | Waldmann |
| 2007/0053536 A1 | 3/2007 | Westerkull |
| 2007/0083078 A1 | 4/2007 | Easter et al. |
| 2007/0100197 A1 | 5/2007 | Perkins et al. |
| 2007/0126540 A1 | 6/2007 | Zimmerling |
| 2007/0170533 A1 | 7/2007 | Doogue et al. |
| 2007/0179333 A1 | 8/2007 | Bove |
| 2007/0208403 A1 | 9/2007 | Della Santina et al. |
| 2008/0009920 A1 | 1/2008 | Gibson et al. |
| 2008/0044049 A1 | 2/2008 | Ho et al. |
| 2008/0071353 A1 | 3/2008 | Weber et al. |
| 2008/0221641 A1 | 9/2008 | Hochmair |
| 2008/0293998 A1 | 11/2008 | Andrews |
| 2008/0304686 A1 | 12/2008 | Meskens et al. |
| 2009/0030529 A1 | 1/2009 | Berrang et al. |
| 2009/0043149 A1 | 2/2009 | Abel |
| 2009/0069869 A1 | 3/2009 | Stouffer et al. |
| 2009/0138062 A1 | 5/2009 | Balslev |
| 2009/0237080 A1 | 9/2009 | Kato et al. |
| 2009/0248155 A1 | 10/2009 | Parker |
| 2009/0251264 A1 | 10/2009 | Fullerton et al. |
| 2009/0281367 A1 | 11/2009 | Cho et al. |
| 2009/0287036 A1 | 11/2009 | Shapiro et al. |
| 2009/0287278 A1 | 11/2009 | Charvin |
| 2009/0295521 A1 | 12/2009 | Fullerton et al. |
| 2010/0145135 A1 | 6/2010 | Ball et al. |
| 2010/0219712 A1 | 9/2010 | Kogure et al. |
| 2010/0237969 A1 | 9/2010 | Crawshaw |
| 2010/0272299 A1 | 10/2010 | Van Schuylenbergh et al. |
| 2010/0292759 A1 | 11/2010 | Hahn et al. |
| 2011/0004278 A1 | 1/2011 | Aghassian |
| 2011/0022120 A1 | 1/2011 | Ball et al. |
| 2011/0031839 A1 | 2/2011 | Fullerton et al. |
| 2011/0054237 A1 | 3/2011 | Shapiro et al. |
| 2011/0077502 A1 | 3/2011 | Rofougaran |
| 2011/0106210 A1 | 5/2011 | Meskens |
| 2011/0112607 A1 | 5/2011 | Zierhofer |
| 2011/0130622 A1 | 6/2011 | Ilberg |
| 2011/0152603 A1 | 6/2011 | Perkins et al. |
| 2011/0224789 A1 | 9/2011 | Griffith |
| 2011/0264172 A1* | 10/2011 | Zimmerling ......... A61N 1/3718 607/60 |
| 2011/0268303 A1 | 11/2011 | Ahsani |
| 2011/0285488 A1 | 11/2011 | Scott et al. |
| 2011/0291507 A1 | 12/2011 | Post |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0062992 A1 | 3/2012 | Kimoto |
| 2012/0078035 A1 | 3/2012 | Andersson et al. |
| 2012/0080039 A1 | 4/2012 | Siegert |
| 2012/0088956 A1 | 4/2012 | Asnes et al. |
| 2012/0095283 A1 | 4/2012 | Andersson et al. |
| 2012/0104875 A1 | 5/2012 | Park |
| 2012/0108887 A1 | 5/2012 | Vermeiren |
| 2012/0172659 A1 | 7/2012 | Ball et al. |
| 2012/0237067 A1 | 9/2012 | Asnes |
| 2012/0238799 A1 | 9/2012 | Ball et al. |
| 2012/0256715 A1 | 10/2012 | Fullerton et al. |
| 2012/0262019 A1 | 10/2012 | Smith et al. |
| 2012/0262020 A1 | 10/2012 | Smith et al. |
| 2012/0284969 A1 | 11/2012 | Fullerton et al. |
| 2012/0296155 A1 | 11/2012 | Ball |
| 2012/0313473 A1 | 12/2012 | Chen et al. |
| 2012/0319809 A1 | 12/2012 | Fullerton |
| 2012/0323066 A1 | 12/2012 | Cho et al. |
| 2012/0330378 A1 | 12/2012 | Crawford et al. |
| 2013/0004003 A1 | 1/2013 | Tada |
| 2013/0006044 A1 | 1/2013 | Menzl |
| 2013/0018218 A1 | 1/2013 | Haller et al. |
| 2013/0023954 A1 | 1/2013 | Meskens |
| 2013/0046131 A1 | 2/2013 | Ball et al. |
| 2013/0046360 A1 | 2/2013 | Gibson et al. |
| 2013/0053874 A1 | 2/2013 | Ekvall et al. |
| 2013/0096366 A1 | 4/2013 | Bervoets et al. |
| 2013/0099703 A1 | 4/2013 | Epstein et al. |
| 2013/0110198 A1 | 5/2013 | Stoffaneller |
| 2013/0113317 A1 | 5/2013 | Englert |
| 2013/0114834 A1 | 5/2013 | Bern |
| 2013/0165738 A1 | 6/2013 | Ball et al. |

(56) References Cited

U.S. PATENT DOCUMENTS

| | | |
|---|---|---|
| 2013/0190552 A1 | 7/2013 | Leblans |
| 2013/0195304 A1 | 8/2013 | Andersson |
| 2013/0199031 A1 | 8/2013 | Fullerton et al. |
| 2013/0202140 A1 | 8/2013 | Asnes |
| 2013/0207760 A1 | 8/2013 | Clarke et al. |
| 2013/0214631 A1 | 8/2013 | Smith et al. |
| 2013/0261701 A1 | 10/2013 | Kuratle et al. |
| 2013/0268012 A1 | 10/2013 | Sison |
| 2013/0278254 A1 | 10/2013 | Reeder et al. |
| 2013/0281764 A1 | 10/2013 | Björn et al. |
| 2013/0289384 A1 | 10/2013 | Jenison et al. |
| 2013/0305522 A1 | 11/2013 | Fullerton et al. |
| 2014/0005522 A1 | 1/2014 | Zurovcik |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1* | 1/2014 | Zimmerling ......... A61N 1/3718 607/57 |
| 2014/0064531 A1 | 3/2014 | Andersson et al. |
| 2014/0094876 A1 | 4/2014 | Wingeier et al. |
| 2014/0121447 A1 | 5/2014 | Kasic et al. |
| 2014/0121450 A1 | 5/2014 | Kasic et al. |
| 2014/0121451 A1 | 5/2014 | Kasic et al. |
| 2014/0163308 A1 | 6/2014 | Miller et al. |
| 2014/0163309 A1 | 6/2014 | Bernhard et al. |
| 2014/0213139 A1 | 7/2014 | Ferguson |
| 2014/0242140 A1 | 8/2014 | Neu et al. |
| 2014/0257081 A1 | 9/2014 | Rapoport |
| 2014/0270297 A1 | 9/2014 | Gustafsson et al. |
| 2014/0275731 A1 | 9/2014 | Andersson et al. |
| 2014/0275736 A1 | 9/2014 | Ruppersberg et al. |
| 2014/0292321 A1 | 10/2014 | Yamazaki et al. |
| 2014/0293073 A1 | 10/2014 | Okamura et al. |
| 2014/0300437 A1 | 10/2014 | Fullerton et al. |
| 2014/0302741 A1 | 10/2014 | Whittaker |
| 2014/0321681 A1 | 10/2014 | Ball et al. |
| 2014/0336447 A1 | 11/2014 | Björn et al. |
| 2014/0343626 A1 | 11/2014 | Thenuwara et al. |
| 2014/0364681 A1 | 12/2014 | Hillbratt et al. |
| 2014/0364682 A1 | 12/2014 | Hillbratt et al. |
| 2014/0364922 A1 | 12/2014 | Garnham et al. |
| 2014/0375829 A1 | 12/2014 | Nishihara et al. |
| 2014/0379103 A1 | 12/2014 | Ishikawa et al. |
| 2015/0022298 A1 | 1/2015 | Fullerton |
| 2015/0032186 A1 | 1/2015 | Cushing et al. |
| 2015/0045607 A1 | 2/2015 | Håkansson |
| 2015/0045855 A1 | 2/2015 | Griffith |
| 2015/0087892 A1 | 3/2015 | Tourrel et al. |
| 2015/0092969 A1 | 4/2015 | Meskens et al. |
| 2015/0104052 A1 | 4/2015 | Gustafsson et al. |
| 2015/0117689 A1 | 4/2015 | Bergs et al. |
| 2015/0156595 A1 | 6/2015 | Zhong et al. |
| 2015/0157778 A1 | 6/2015 | Ishiyama et al. |
| 2015/0160426 A1 | 6/2015 | Chao et al. |
| 2015/0160470 A1 | 6/2015 | Terajima |
| 2015/0173468 A1 | 6/2015 | Stevenson |
| 2015/0192432 A1 | 7/2015 | Noguchi et al. |
| 2015/0201290 A1 | 7/2015 | Nikles et al. |
| 2015/0215708 A1 | 7/2015 | Meskens et al. |
| 2015/0265842 A1 | 9/2015 | Ridler et al. |
| 2015/0281860 A1 | 10/2015 | Johansson et al. |
| 2015/0312686 A1 | 10/2015 | Gustafsson et al. |
| 2015/0382114 A1 | 12/2015 | Andersson et al. |
| 2016/0021470 A1 | 1/2016 | Gustafsson |
| 2016/0037273 A1 | 2/2016 | Gustafsson |
| 2016/0058555 A1 | 3/2016 | Andersson et al. |
| 2016/0084920 A1 | 3/2016 | Liu et al. |
| 2016/0100260 A1 | 4/2016 | Ruppersberg et al. |
| 2016/0112813 A1 | 4/2016 | Hillbratt et al. |
| 2016/0161288 A1 | 6/2016 | Lu |
| 2016/0198270 A9 | 7/2016 | Nagl et al. |
| 2016/0205484 A1 | 7/2016 | Nagl et al. |
| 2016/0234613 A1 | 8/2016 | Westerkull |
| 2016/0247616 A1 | 8/2016 | Smith et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0078808 A1* | 3/2017 | Kennes ................ H05K 999/99 |
| 2017/0111728 A1 | 4/2017 | Kim et al. |
| 2017/0117087 A1* | 4/2017 | Ridler ................ A61N 1/36036 |
| 2017/0162311 A1 | 6/2017 | Shmbo et al. |
| 2017/0162367 A1 | 6/2017 | Yokota et al. |
| 2017/0180891 A1 | 6/2017 | Johansson |
| 2017/0216523 A1 | 8/2017 | Neftel et al. |
| 2017/0251313 A1 | 8/2017 | Gustafsson |
| 2018/0160241 A1 | 6/2018 | Gustafsson et al. |
| 2018/0252228 A1 | 9/2018 | Henseler et al. |
| 2018/0270591 A1 | 9/2018 | Kennes |
| 2018/0288538 A1 | 10/2018 | Andersson et al. |
| 2018/0352349 A1 | 12/2018 | Fung et al. |
| 2018/0369586 A1 | 12/2018 | Lee et al. |
| 2019/0046797 A1 | 2/2019 | Calixto et al. |
| 2019/0076649 A1 | 3/2019 | Lee et al. |
| 2019/0151653 A1 | 5/2019 | Leigh et al. |
| 2019/0215623 A1 | 7/2019 | Bodvarsson |
| 2019/0239007 A1* | 8/2019 | Kennes ................ H04R 25/60 |
| 2019/0293454 A1 | 9/2019 | Bidaux et al. |
| 2020/0114151 A1 | 4/2020 | Smith et al. |
| 2020/0197702 A1 | 6/2020 | Eigentler |
| 2021/0046318 A1 | 2/2021 | Gibson et al. |
| 2021/0106815 A1 | 4/2021 | Smith et al. |
| 2021/0235209 A1 | 7/2021 | Kennes et al. |
| 2021/0257139 A1 | 8/2021 | Nellessen |
| 2021/0316136 A1 | 10/2021 | Smith et al. |
| 2022/0072302 A1 | 3/2022 | Zimmerling |
| 2023/0031813 A1 | 2/2023 | Leigh |

FOREIGN PATENT DOCUMENTS

| | | |
|---|---|---|
| CN | 103781008 A | 5/2014 |
| EP | 2720480 A2 | 4/2014 |
| EP | 3307383 B1 | 3/2020 |
| GB | 414579 A | 8/1934 |
| GB | 2196855 A | 5/1988 |
| GB | 2205999 A | 12/1988 |
| GB | 2266045 A | 10/1993 |
| JP | 2010075394 A | 4/2010 |
| JP | 2012191448 A | 10/2012 |
| JP | 2013232860 A | 11/2013 |
| KR | 101297828 B1 | 8/2013 |
| KR | 101537380 B1 | 7/2015 |
| KR | 10-1743793 | 6/2017 |
| WO | 9716835 A1 | 5/1997 |
| WO | 9939769 A1 | 8/1999 |
| WO | 2007024657 A1 | 3/2007 |
| WO | 2014008169 A1 | 1/2014 |
| WO | 2014011582 A2 | 1/2014 |
| WO | 2015065442 A2 | 5/2015 |
| WO | 2016207856 A1 | 12/2016 |
| WO | 2016207860 A1 | 12/2016 |
| WO | 2017046650 A1 | 3/2017 |
| WO | 2017105510 A1 | 6/2017 |
| WO | 2017105511 A1 | 6/2017 |
| WO | 2018200347 A1 | 11/2018 |
| WO | 2021059163 A1 | 4/2021 |

OTHER PUBLICATIONS

MED-EL, "FDA Hands MED-EL Approval for MRI Compatible Cochlear Implant (VIDEO)," believed to be available in Jan. 2015.
Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.
Extended European Search Report for European Patent Application No. 23 159 644.6, mailed Jun. 12, 2023.
Extended European Search Report for European Patent Application No. 20 868 236.9, mailed Jun. 9, 2023.
Extended Search Report for EU Patent Application No. 15 828 071.9, mailed Feb. 12, 2018.
International Search Report and Written Opinion for PCT/IB2015/055733, mailed Nov. 10, 2015.
Office Action for CN Application No. 2016800371371, mailed Mar. 11, 2020.

(56) References Cited

OTHER PUBLICATIONS

Extended European Search Report for EP Application No. 168138303, mailed Jan. 29, 2019.
Extended European search report for European Patent Application No. 23 210 962.9, mailed Jun. 12, 2024.
International Search Report and Written Opinion for PCT/IB2016/053787, mailed Sep. 30, 2016

* cited by examiner

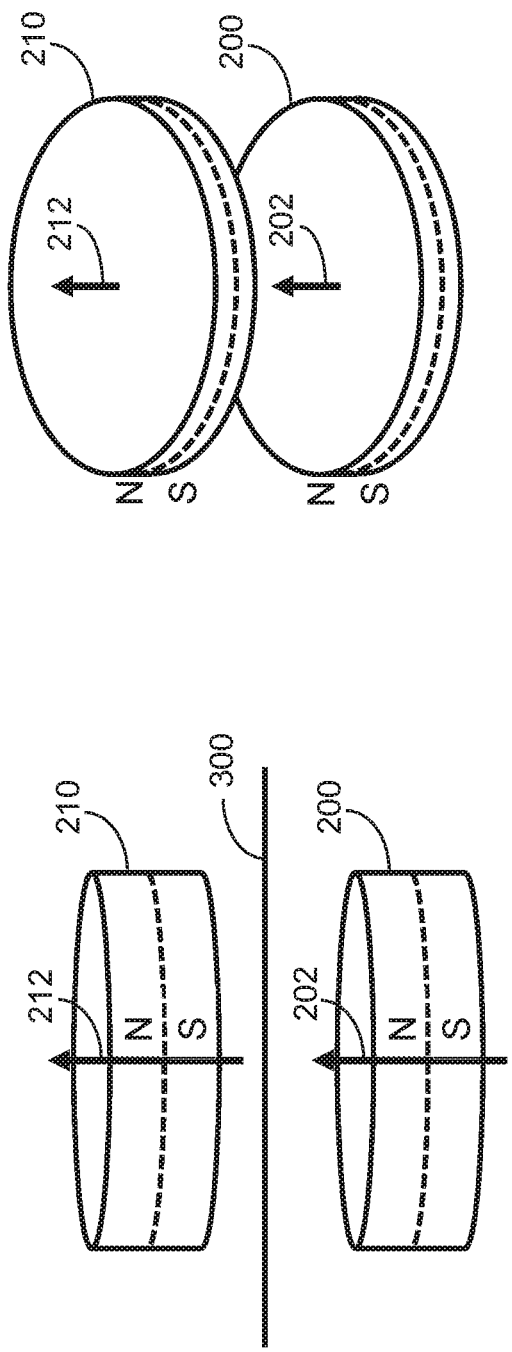
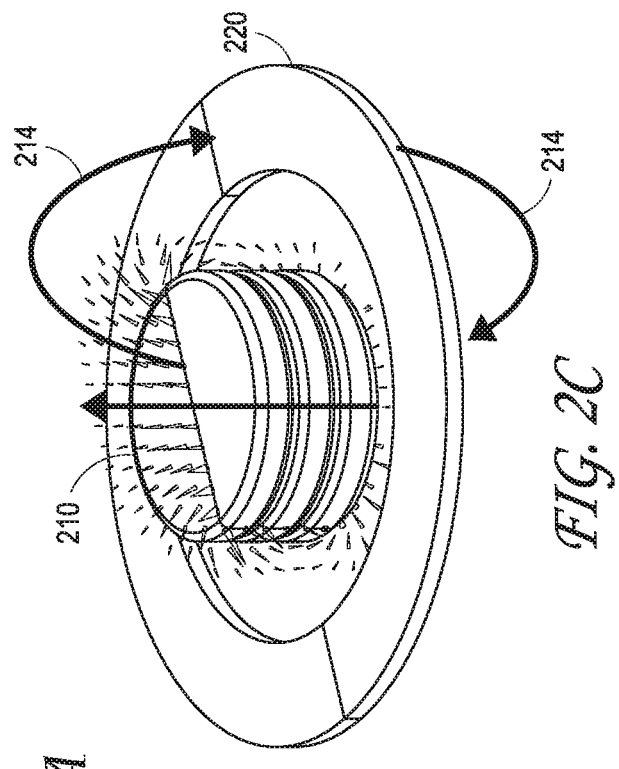
FIG. 2A
FIG. 2B
FIG. 2C

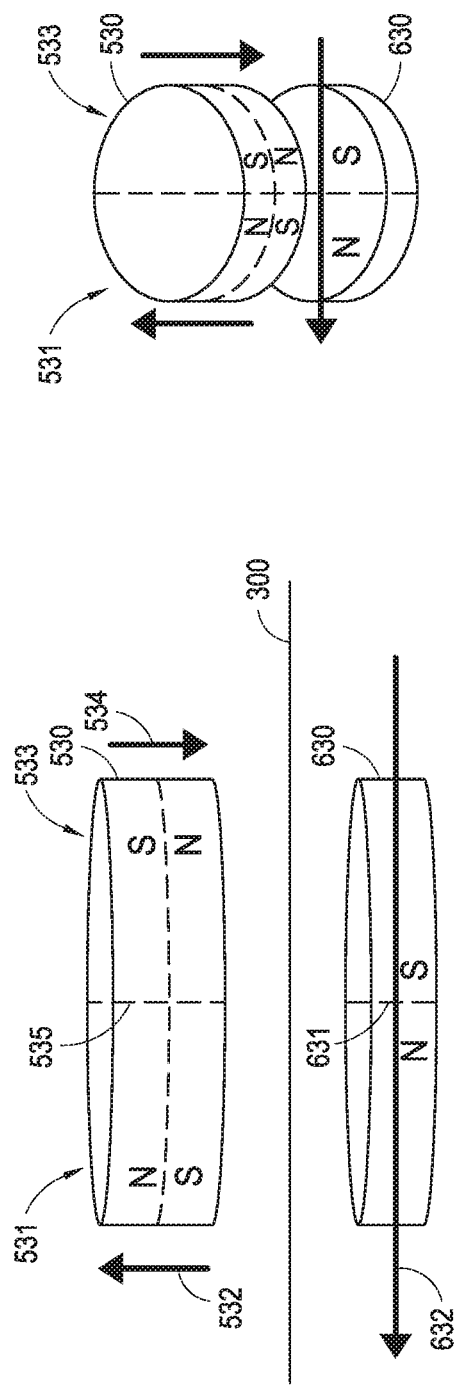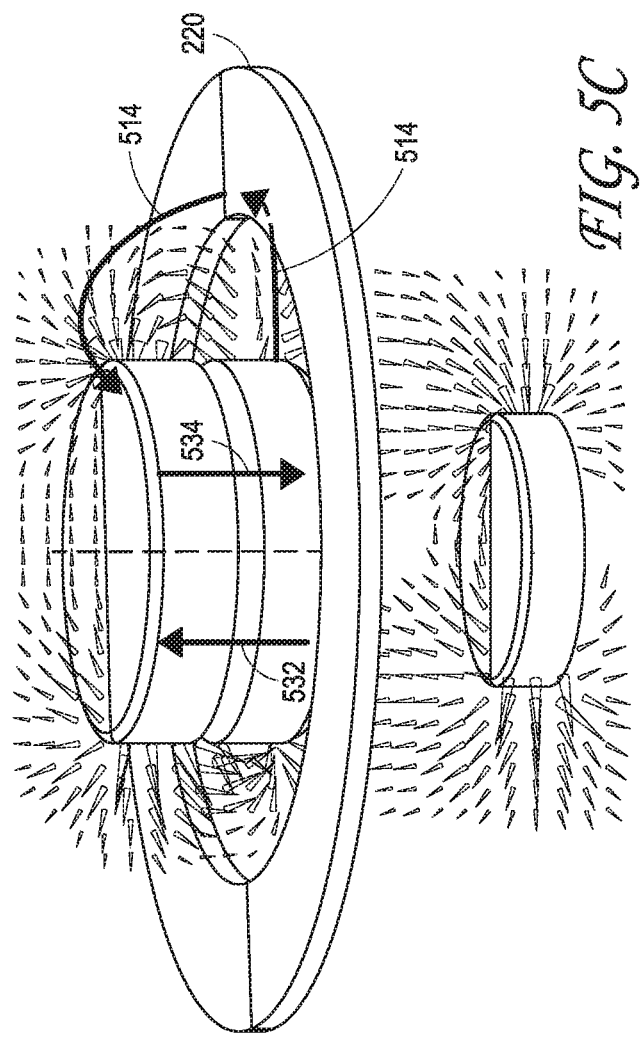

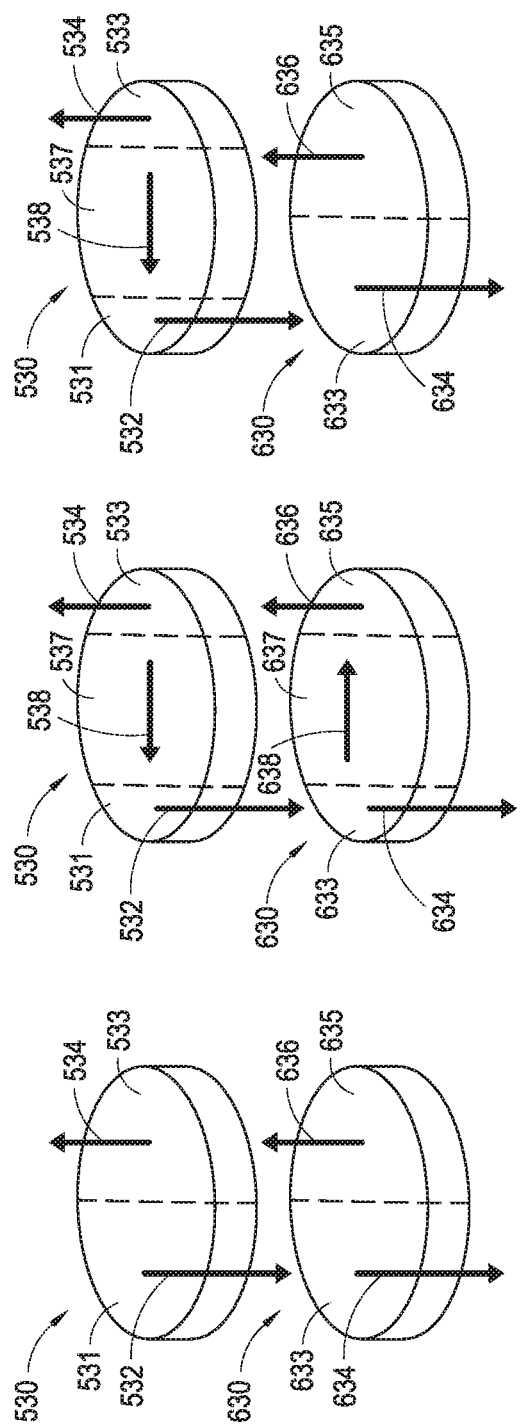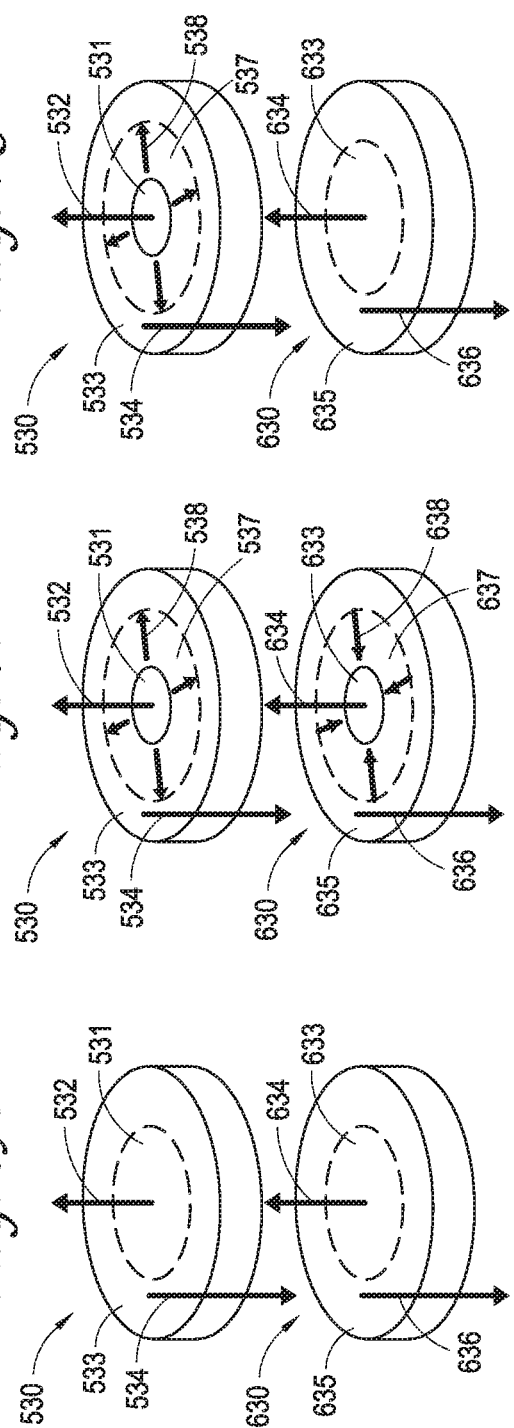

MULTIPOLE MAGNET FOR MEDICAL IMPLANT SYSTEM

BACKGROUND

Field

The present application relates generally to implantable medical systems, and more specifically to magnets for transcutaneously mechanically coupling an external portion of a medical system with an implanted portion of the medical system.

Description of the Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect disclosed herein, an apparatus is provided which comprises a housing configured to be placed over a portion of skin of a recipient, the portion of skin overlaying an implanted device. The apparatus further comprises circuitry within the housing. The circuitry is configured to wirelessly communicate with the implanted device. The apparatus further comprises a unitary magnet in mechanical communication with the housing. The magnet comprises at least one first magnetic dipole moment having a first magnitude and a first direction and at least one second magnetic dipole moment having a second magnitude substantially equal to the first magnitude and a second direction substantially opposite to the first direction.

In another aspect disclosed herein, an assembly is configured to be placed over a portion of skin of a recipient overlaying an implanted device. The assembly comprises at least one planar external inductive communication coil configured to be in inductive communication with at least one internal inductive communication coil of the implanted device. The assembly further comprises at least one planar ferrite component positioned above and parallel to the at least one planar external inductive communication coil. The assembly further comprises a monolithic magnet comprising a plurality of magnetized portions with different magnetizations from one another. The magnet is configured to produce a magnetic field configured to interact with the implanted device to provide sufficient magnetic force to retain the assembly over the implanted device. The magnetic field is substantially perpendicularly intersecting the at least one planar ferrite component.

In still another aspect disclosed herein an apparatus is provided which comprises a housing configured to be implanted beneath a portion of skin of a recipient. The apparatus further comprises circuitry within the housing. The circuitry is configured to wirelessly communicate with an external device overlaying the portion of skin. The apparatus further comprises a unitary magnet within the housing. The magnet comprises at least one first magnetic dipole moment having a first magnitude and a first direction and at least one second magnetic dipole moment having a second magnitude substantially equal to the first magnitude and a second direction substantially opposite to the first direction.

BRIEF DESCRIPTION OF THE DRAWINGS

Embodiments are described herein in conjunction with the accompanying drawings, in which:

FIGS. 2A-2B schematically illustrate two perspective views of a first example configuration of an implanted magnet and an external magnet;

FIG. 2C schematically illustrates a perspective view of a portion of the magnetic field of the external magnet of FIGS. 2A-2B;

FIGS. 5A-5B schematically illustrate perspective views of an example external magnet and an internal magnet in accordance with certain embodiments described herein;

FIG. 5C schematically illustrates the magnetic field of the external magnet of FIGS. 5A-5B in relation to at least one planar ferrite component in accordance with certain embodiments described herein;

FIGS. 7A-7F schematically illustrate various example configurations of an external magnet and an internal magnet in accordance with certain embodiments described herein.

DETAILED DESCRIPTION

Certain embodiments described herein advantageously utilize a magnet of an external transmitter unit of an implantable medical device system, the external transmitter unit comprising at least one external inductive communication coil and a ferrite component configured to shield other components of the external transmitter unit from magnetic fields generated by the at least one external inductive communication coil. The implantable medical device system is advantageously compatible with magnetic resonance imaging (MRI), the magnet does not adversely affect (e.g., interfere with; degrade) operation of other components of the external transmitter unit, and the magnet is compatible with implanted devices comprising a diametrically magnetized implanted magnet. The magnet of certain such embodiments comprises a unitary (e.g., monolithic) body and has a plurality of portions, each portion having a corresponding magnetization (e.g., a magnetic dipole moment). The magnetizations are oriented relative to one another to provide a magnetic field that substantially perpendicularly intersects the ferrite component of the external transmitter unit.

The teachings detailed herein are applicable, in at least some embodiments, to any type of implantable medical device, for example, auditory prosthesis utilizing an implantable actuator assembly including but not limited to: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Embodiments can include any type of medical device that can utilize the teachings detailed herein and/or variations thereof. In some embodiments, the teachings detailed herein and/or variations thereof can be utilized in other types of implantable medical devices beyond auditory prostheses. For example, the concepts described herein can be applied to any of a variety of implantable medical devices that utilize the transfer of power and/or data between an implanted component and an external component via inductive coupling (e.g., pacemakers; implantable EEG monitoring devices; visual prostheses).

Figure 1:
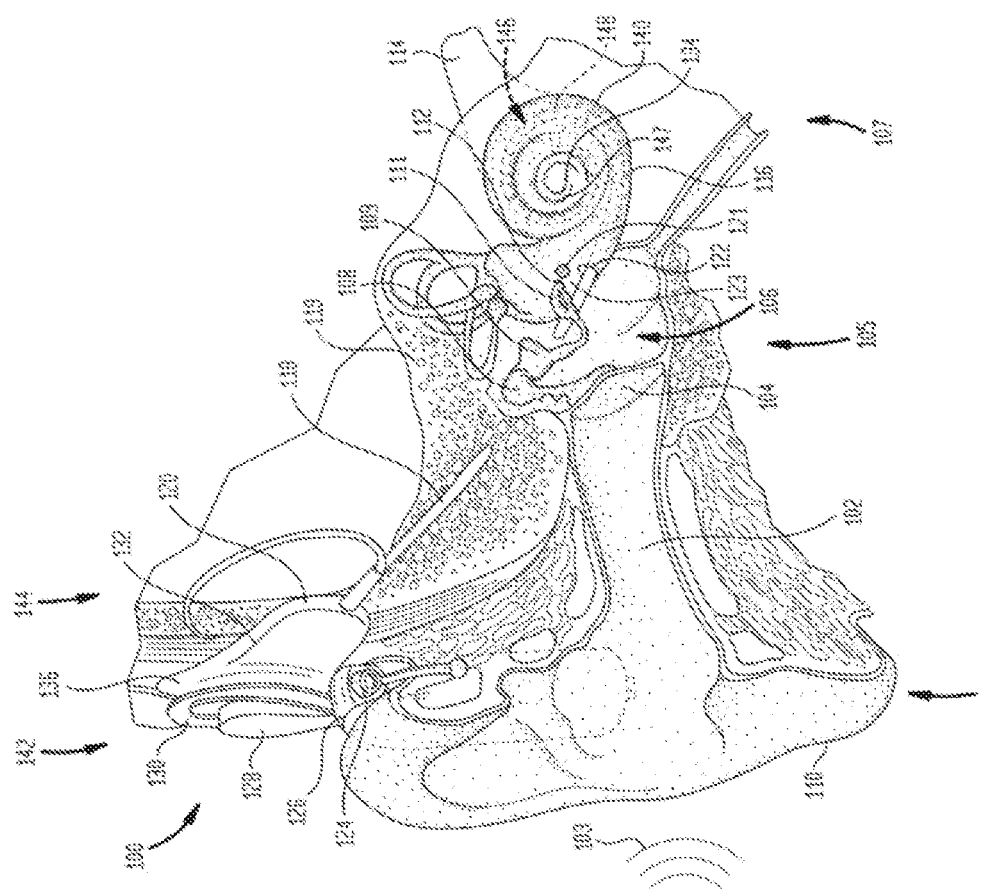
FIG. 1 is a perspective view of an example cochlear implant auditory prosthesis implanted in a recipient in accordance with certain embodiments described herein.

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a totally implantable cochlear implant) in accordance with certain embodiments described herein can replace the external microphone assembly 124 shown in FIG. 1 with a subcutaneously implantable assembly comprising an acoustic transducer (e.g., microphone), as described more fully herein.

As shown in FIG. 1, the recipient normally has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within the cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more input elements/devices for receiving input signals at a sound processing unit 126. The one or more input elements/devices can include one or more sound input elements (e.g., one or more external microphones 124) for detecting sound and/or one or more auxiliary input devices (not shown in FIG. 1)(e.g., audio ports, such as a Direct Audio Input (DAI); data ports, such as a Universal Serial Bus (USB) port; cable ports, etc.). In the example of FIG. 1, the sound processing unit 126 is a behind-the-ear (BTE) sound processing unit configured to be attached to, and worn adjacent to, the recipient's ear. However, in certain other embodiments, the sound processing unit 126 has other arrangements, such as by an OTE processing unit (e.g., a component having a generally cylindrical shape and which is configured to be magnetically coupled to the recipient's head), etc., a mini or micro-BTE unit, an in-the-canal unit that is configured to be located in the recipient's ear canal, a body-worn sound processing unit, etc.

The sound processing unit 126 of certain embodiments includes a power source (not shown in FIG. 1)(e.g., battery), a processing module (not shown in FIG. 1)(e.g., comprising one or more digital signal processors (DSPs), one or more microcontroller cores, one or more application-specific integrated circuits (ASICs), firmware, software, etc. arranged to perform signal processing operations), and an external transmitter unit 128. In the illustrative embodiments of FIG. 1, the external transmitter unit 128 comprises circuitry that includes at least one external inductive communication coil 130 (e.g., a wire antenna coil comprising multiple turns of electrically insulated single-strand or multi-strand platinum or gold wire). The external transmitter unit 128 also generally comprises a magnet (not shown in FIG. 1) secured directly or indirectly to the at least one external inductive communication coil 130. The at least one external inductive communication coil 130 of the external transmitter unit 128 is part of an inductive radio frequency (RF) communication link with the internal component 144. The sound processing unit 126 processes the signals from the input elements/devices (e.g., microphone 124 that is positioned externally to the recipient's body, in the depicted embodiment of FIG. 1, by the recipient's auricle 110). The sound processing unit 126 generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing, sometimes collectively referred to as a stimulator/receiver unit. The internal receiver unit 132 comprises at least one internal inductive communication coil 136 (e.g., a wire antenna coil comprising multiple turns of electrically insulated single-strand or multi-strand platinum or gold wire), and generally, a magnet (not shown in FIG. 1) fixed relative to the at least one internal inductive communication coil 136. The at least one internal inductive communication coil 136 receives power and/or data signals from the at least one external inductive communication coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 can be implanted at least in the basal region 116, and sometimes further. For example, the electrode assembly 118 can extend towards an apical end of the cochlea 140, referred to as the cochlea apex 134. In certain circumstances, the electrode assembly 118 can be inserted into the cochlea 140 via a cochleostomy 122. In other circumstances, a cochleostomy can be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

FIGS. 2A-2B schematically illustrate two perspective views of a first example configuration of an implanted magnet 200 (e.g., enclosed in an internal component 144 of an auditory prosthesis implanted beneath the recipient's skin 300) and an external magnet 210 (e.g., enclosed in an external component 142 of the auditory prosthesis outside or on the recipient's skin 300). The implanted magnet 200 has a magnetization comprising a single implanted magnetic dipole moment 202 and the external magnet 210 has a magnetization comprising a single external magnetic dipole moment 212 with a direction substantially parallel to and in the same direction as the single implanted magnetic dipole moment 202. Each of the implanted magnet 200 and the external magnet 210 has a right circular cylindrical shape with a center axis and the respective magnetizations are substantially parallel to the respective center axes (e.g., the implanted magnet 200 and the external magnet 210 are axially magnetized) and the respective magnetizations are substantially perpendicular to the recipient's skin 300. By having the respective axial magnetizations aligned with one another, the external magnet 210 provides sufficient retention to the implanted magnet 200 to keep the external component 142 in an operational position relative to the internal component 144.

However, the orientation of the single implanted magnetic dipole moment 202 of the implanted magnet 200 (e.g., substantially perpendicular to the recipient's skin 300 as shown in the example configuration of FIGS. 2A and 2B) has been described as being incompatible with magnetic-resonance imaging (MRI) since the magnetically-induced torque ($\vec{\tau} = \vec{m} \times \vec{B}$) on the implanted magnet 200 due to the large MRI magnetic fields interacting with the single implanted magnetic dipole moment 202 is potentially detrimental (e.g., resulting in pain to the recipient and/or damage to the recipient and/or the auditory prosthesis).

FIG. 2C schematically illustrates a perspective view of a portion of the magnetic field 214 of the external magnet 210 of FIGS. 2A-2B. For example, the external magnet 210 can be a component of an external transmitter unit 128 comprising circuitry with at least one external inductive communication coil 130 (not shown in FIG. 2C) and a ferrite component 220 having a generally planar shape, positioned above and parallel to the at least one external inductive communication coil 130, and configured to shield other components of the circuitry of the external transmitter unit 128 from magnetic fields generated by the at least one external inductive communication coil 130. The magnetic field 214 of the external magnet 210 extends to and substantially perpendicularly intersects the ferrite component 220, such that the magnetic field 214 does not saturate the ferrite component 220 (e.g., does not reduce the shielding provided by the ferrite component 220 of the other components of the circuitry of the external transmitter unit 128 from the magnetic fields generated by the at least one external inductive communication coil 130).

Figure 3A:
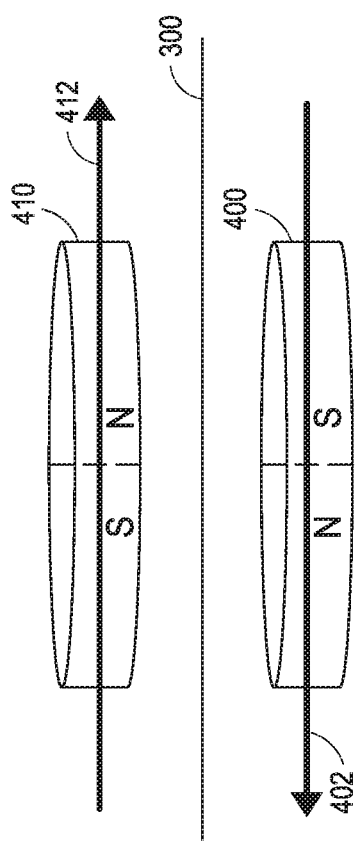
FIGS. 3A-3B schematically illustrate two perspective views of a second example configuration of an implanted magnet and an external magnet.
Figure 3B:
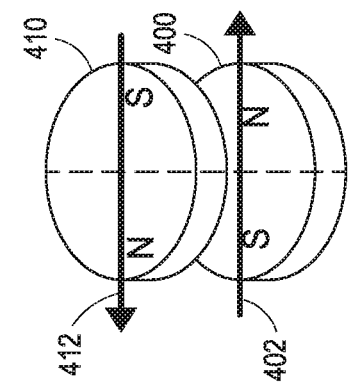

FIGS. 3A-3B schematically illustrate two perspective views of a second example configuration of an implanted magnet 400 (e.g., enclosed in an internal component 144 of an auditory prosthesis implanted beneath the recipient's skin 300) and an external magnet 410 (e.g., enclosed in an external component 142 of the auditory prosthesis outside or on the recipient's skin 300). The implanted magnet 400 has a magnetization comprising a single implanted magnetic dipole moment 402 and the external magnet 410 has a magnetization comprising a single external magnetic dipole moment 412 with a direction substantially parallel to and in the opposite direction as the single implanted magnetic dipole moment 402. Each of the implanted magnet 400 and the external magnet 410 has a right circular cylindrical shape with a center axis and the respective magnetizations are substantially perpendicular to the respective center axes (e.g., the implanted magnet 400 and the external magnet 410 are diametrically magnetized) and the respective magnetizations are substantially parallel to the recipient's skin 300.

By having the respective diametrical magnetizations aligned with one another, the external magnet 410 provides sufficient retention to the implanted magnet 400 to keep the external component 142 in an operational position relative to the internal component 144.

In contrast to the example configuration of FIGS. 2A-2C, the orientation of the single implanted magnetic dipole moment 402 of the implanted magnet 400 (e.g., substantially parallel to the recipient's skin 300 as shown in the example configuration of FIGS. 3A and 3B) has been described as being compatible with MRI since the magnetically-induced torque ($\vec{\tau}=\vec{m}\times\vec{B}$) on the implanted magnet 400 due to the large MRI magnetic fields interacting with the single implanted magnetic dipole moment 402 has a lower magnitude than in FIGS. 2A-2C, and is less likely to be potentially detrimental (e.g., resulting in pain to the recipient and/or damage to the recipient and/or the auditory prosthesis). In addition, the orientation of the single external magnetic dipole moment 412 of the external magnet 410 (e.g., substantially parallel to the recipient's skin 300 as shown in the example configuration of FIGS. 3A and 3B) is also compatible with MRI since the resulting magnetically-induced torque on the external magnet 210 is less likely to be potentially detrimental than in the example configuration of FIGS. 2A-2C.

Figure 3C:
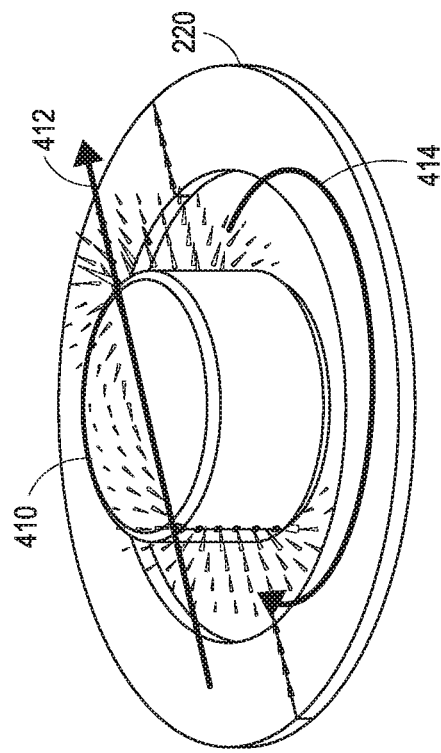
FIG. 3C schematically illustrates a perspective view of a portion of the magnetic field of the external magnet of FIGS. 3A-3B.

FIG. 3C schematically illustrates a perspective view of a portion of the magnetic field 414 of the external magnet 410 of FIGS. 3A-3B. For example, the external magnet 410 can be a component of an external transmitter unit 128 comprising circuitry with at least one external inductive communication coil 130 (not shown in FIG. 3C) and the generally planar ferrite component 220 configured to shield other components of the circuitry of the external transmitter unit 128 from magnetic fields generated by the at least one external inductive communication coil 130. The magnetic field 414 of the external magnet 410 extends to and is substantially parallel to the ferrite component 220. As a result, the magnetic field 414 can saturate the ferrite component 220 (e.g., can reduce the shielding provided by the ferrite component 220 of the other components of the circuitry of the external transmitter unit 128 from the magnetic fields generated by the at least one external inductive communication coil 130). In this way, the magnetic field 414 of the external magnet 410 in the example configuration of FIGS. 3A-3C can extend a significant distance away from the external magnet 410 and can interfere with other components of the circuitry of the external transmitter unit 128, potentially adversely affecting operation of the circuitry (e.g., interfering with the inductive RF link to the internal component 144). Such interference can result in various adverse effects, including but not limited to: reduction in the battery life of the auditory prosthesis 100 and/or sound processing unit 126 (e.g., by 30%), increase in the RF link power consumption, increased RF tuning range, and reduced coil alignment tolerance for inductive charging.

Some previous systems have sought to address the unwanted magnetic fields of the external magnet by using a magnetic flux guide (e.g., cylindrical or can-shaped; comprising "mu-metal" or other materials with sufficiently high magnetic permittivity) between the external magnet and the circuitry of the external transmitter unit 128 to direct the magnetic field away from key components of the circuitry (see, e.g., U.S. Pat. No. 9,392,384). However, such structures undesirably add mass and volume to the external transmitter unit 128. Other previous systems have used an external magnet comprising a modified Halbach array to reduce unwanted magnetic fields (see, e.g., U.S. Pat. Appl. Publ. No. 2017/0078808). However, such structures can utilize undesirably larger diameters for the magnet assembly of the external transmitter unit 128.

Figure 4:
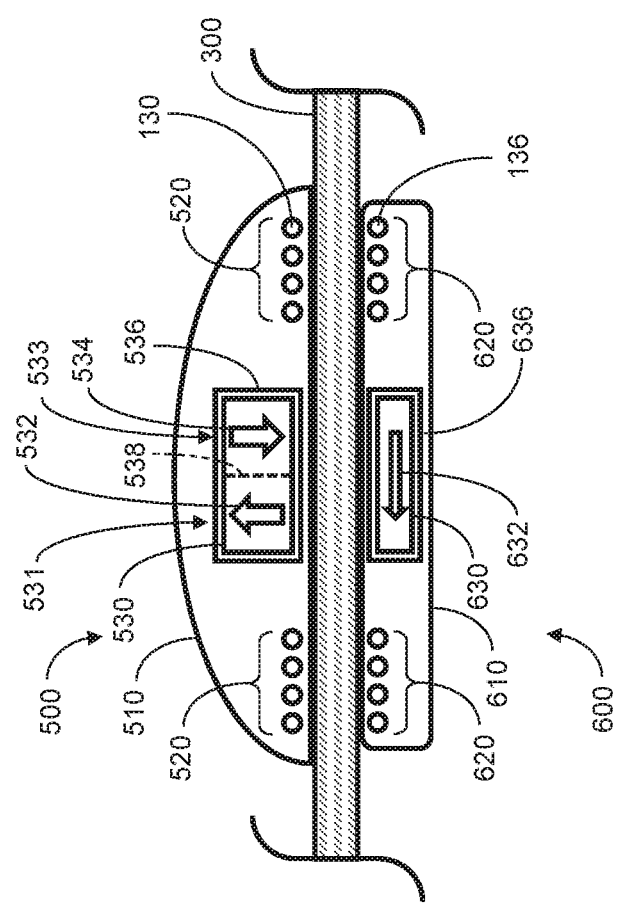
FIG. 4 schematically illustrates a cross-sectional view of an example apparatus in accordance with certain embodiments described herein.

FIG. 4 schematically illustrates a cross-sectional view of an example apparatus 200 in accordance with certain embodiments described herein. The apparatus 500 comprises a housing 510 configured to be placed over a portion of skin 300 of a recipient. The portion of skin 300 overlays an implanted device 600. The apparatus 500 further comprises circuitry 520 within the housing 510, the circuitry 520 configured to wirelessly communicate with the implanted device 600. The apparatus 500 further comprises a unitary magnet 530 (e.g., a monolithic magnet) in mechanical communication with the housing 510. The magnet 530 comprises at least one first magnetic dipole moment 532 having a first magnitude and a first direction and at least one second magnetic dipole moment 534 having a second magnitude substantially equal to the first magnitude and a second direction substantially opposite to the first direction. In certain embodiments, the at least one first dipole magnetic moment 532 and the at least one second magnetic dipole moment 534 are configured to produce an external magnetic field configured to, when the housing 510 is placed over the portion of the skin 300, attract the magnet 530 to the implanted device 600 while not adversely affecting operation of the circuitry 520.

In certain embodiments, the apparatus 500 is an external component 142 of an implantable medical device (e.g., an auditory prosthesis system; a cochlear implant auditory prosthesis 100 as schematically illustrated by FIG. 1), and the internal device 600 is an internal component 144 of the implantable medical device. For example, the apparatus 500 can be an external component 142 of an auditory prosthesis system selected from the group consisting of: a cochlear implant system, a Direct Acoustic Cochlear Implant (DACI) system, a middle ear implant system, a middle ear transducer (MET) system, an electro-acoustic implant system, another type of auditory prosthesis system, and/or combinations or variations thereof.

In certain embodiments, the external component 142 can comprise the housing 510 (e.g., comprising a polymer material and/or other material compatible for being placed in contact with the recipient's skin 300), the circuitry 520 (e.g., comprising at least one microphone 124, a sound processing unit 126, a power source, an external transmitter unit 128, and/or the at least one external inductive communication coil 130, as schematically illustrated by FIG. 1) within the housing 510, and the magnet 530 which can be in mechanical communication with the housing 510. For example, the magnet 530 can be contained within a cavity 536 of the housing 510 (e.g., as schematically illustrated by FIG. 4), while in other examples, the magnet 530 can be affixed to an exterior portion of the housing 510 and/or can form part of an external surface of the housing 510.

In certain embodiments, the magnet 530 comprises at least one ferromagnetic material selected from the group consisting of: iron, nickel, cobalt, and steel. The magnet 530 of certain embodiments comprises a permanent multipole magnet (e.g., a magnet having two or more portions with different magnetizations) having an external static magnetic field. The magnet 530 of certain embodiments is a non-separable unitary (e.g., monolithic) member (e.g., such that at least one first portion 531 comprising the at least one first magnetic dipole moment 532 and at least one second portion 533 comprising the at least one second magnetic dipole moment 534 cannot be easily separated from one another without damaging the magnet 530). In certain other embodiments, the magnet 530 is a separable unitary (e.g., monolithic) member (e.g., configured to be separated into multiple portions at selected times without damaging the magnet 530). For example, the separable unitary (e.g., monolithic) member can be separated into multiple portions when the magnet 530 is not mounted on or within the housing 510 and can be joined or rejoined together prior to being placed in mechanical communication with the other portions of the apparatus 500 (e.g., the first portion 531 and the second portion 533 are configured to be repeatedly and reversibly separated from one another and repeatedly and reversibly rejoined to one another without damaging the magnet 530).

In certain embodiments, the magnet 530 has a first width that is substantially parallel to the portion of skin 300 upon (e.g., after) placement of the apparatus 500 over the portion of skin 300 (e.g., during operation of the circuitry 520) and a first height that is substantially perpendicular to the portion of skin 300 upon (e.g., after) placement of the apparatus 500 over the portion of skin 300 (e.g., during operation of the circuitry 520). In certain embodiments, the magnet 530 has a cylindrical shape with a cross-section (e.g., circular; elliptical; square; rectangular; polygonal; geometric; irregular; symmetric; non-symmetric) with straight, curved, or irregular sides. For example, the magnet 530 can have a right circular cylindrical shape in which the first width is a first diameter $D_1$, the first height $H_1$ is substantially perpendicular to the first diameter, and having a first circumference $C_1$ ($=\pi D_1$). The magnet 530 of certain embodiments has an orientation during operation of the apparatus 500 (e.g., during operation of the circuitry 520) such that the first diameter $D_1$ is substantially parallel to the recipient's skin 300 and the first height $H_1$ is substantially perpendicular to the recipient's skin 300. The first diameter $D_1$ of certain embodiments is in a range of 10 millimeters to 14 millimeters, and the first height $H_1$ of certain embodiments is in a range of 0.8 millimeter to 8 millimeters (e.g., selected to provide sufficient magnetic attractive force across the skin flap thickness of the recipient). In certain other embodiments, the magnet 530 has a rectangular prism or a hexagonal prism shape, and other shapes and/or sizes of the magnet 530 are also compatible with certain embodiments described herein. In certain embodiments, the magnet 530 has a non-symmetric shape such that the magnet 530 is configured to be contained within the housing 210 in a limited number of orientations (e.g., keyed to only one orientation).

In certain embodiments, the example internal component 144 can comprise an implantable housing 610 (e.g., comprising titanium and/or other biocompatible material compatible for being implanted beneath the recipient's skin 300), circuitry 620, and an internal magnet 630 having at least one third magnetic dipole moment 632. The circuitry 620 of the implantable device 600 can comprise an implanted receiver unit 132, a stimulator unit 120 (e.g., in operative communication with an elongate electrode assembly 118), and/or the at least one internal inductive communication coil 136, as schematically illustrated by FIG. 1. For example, the internal magnet 630 and/or the circuitry 620 of the internal device 600 can be contained within one or more cavities 636 (e.g., hermetically sealed regions) of the implantable housing 610.

As schematically illustrated by FIG. 4, the at least one external inductive communication coil 130 can comprise a first planar inductor coil having a first plurality of turns and the first planar inductor coil can encircle the magnet 530 and/or can encircle a projection of the magnet 530 onto a plane defined by the first planar inductor coil. In addition, as schematically illustrated by FIG. 4, the at least one internal inductive communication coil 136 can comprise a second planar inductor coil having a second plurality of turns and the second planar inductor coil can encircle the internal magnet 630 and/or can encircle a projection of the internal magnet 630 onto a plane defined by the second planar inductor coil.

In certain embodiments, the magnet 530 and the internal magnet 630 are configured to be magnetically attracted to one another with the recipient's skin 300 therebetween. The magnet 530 is positioned relative to the at least one external inductive communication coil 130 such that, when the apparatus 500 is placed in its operational position above the implanted device 600 (e.g., as schematically illustrated by FIG. 4), the magnet 530 is attracted to the implanted magnet 630 and the magnet 530 is configured to position the apparatus 500 such that the at least one external inductive communication coil 130 is aligned with (e.g., centered over; concentric with and over) the at least one internal inductive communication coil 136. As used herein, the term "concentric" refers to the relative positions of the centers of two or more components, and does not refer to any particular shapes of these components (e.g., the magnet 530 and the at least one external inductive communication coil 130 can be concentric with one another without either the magnet 530 or the at least one external inductive communication coil 130 having a circular shape).

In certain embodiments, when the apparatus 500 and the magnet 530 are placed in their operational positions, the magnet 530 is sufficiently close to the implanted magnet 630 such that the magnet 530 and the implanted magnet 630 are magnetically attracted to one another, and the at least one external inductive communication coil 130 within the housing 510 is configured to be in inductive communication with the at least one internal inductive communication coil 136 of the implanted device 600. In certain such embodiments, the at least one external inductive communication coil 130 and the at least one internal inductive communication coil 136 form a transcutaneous inductive radio frequency (RF) communication link between the apparatus 500 and the implanted device 600 (e.g., the inductive communication coils 130, 136 interact with one another via magnetic flux of one of the inductive communication coils 130, 136 passing through the other one of the inductive communication coils 130, 136), across which the implanted device 600 receives power and/or data signals from the apparatus 500. In certain embodiments, when the apparatus 500 and the magnet 530 are placed in their operational positions, the at least one external inductive communication coil is centered over the at least one internal inductive communication coil. For example, a center axis of the at least one external inductive communication coil 130 (e.g., coincident with an axis of symmetry of the shape of the magnet 530 and/or an axis of symmetry of a magnetic field produced by the magnet 530) can be coincident with a center axis of the at least one internal inductive communication coil 136 (e.g., coincident with an axis of symmetry of the shape of the implanted magnet 630 and/or an axis of symmetry of a magnetic field produced by the implanted magnet 630).

FIGS. 5A-5B schematically illustrate perspective views of an example external magnet 530 and an internal magnet 630 in accordance with certain embodiments described herein. The external magnet 530 and the internal magnet 630 are configured to be positioned with the recipient's skin 300 therebetween. The internal magnet 630 of FIGS. 5A-5B has a magnetization that comprises a single magnetic dipole moment 632 that is substantially parallel to the recipient's skin 300 and is oriented substantially perpendicular to a center axis 631 of the internal magnet 630 (e.g., the implanted magnet 630 is diametrically magnetized).

The external magnet 530 of FIGS. 5A-5B has a right circular cylindrical shape having a first diameter and a first height, and the external magnet 530 comprises a first magnetized portion 531 having a first magnetization comprising a first magnetic dipole moment 532 (e.g., the first portion 531 generating the first magnetic dipole moment 532) and a second magnetized portion 533 having a second magnetization comprising a second magnetic dipole moment 534 different from the first magnetization (e.g., the second portion 533 generating the second magnetic dipole moment 534). For example, in FIGS. 5A-5B, the first magnetized portion 531 comprises a first half of the external magnet 530, the second magnetized portion 533 comprises a second half of the external magnet 530, and the second magnetic dipole moment 534 has a magnitude substantially equal to the magnitude of the first magnetic dipole moment 532 and a second direction which is substantially parallel and opposite to a first direction of the first magnetic dipole moment 534. The external magnet 530 of FIGS. 5A-5B is configured to be mounted to the housing 510 such that the first and second magnetic dipole moments 532, 534 are substantially perpendicular to the portion of skin 300 during operation of the apparatus 500 (e.g., during operation of the circuitry 520).

FIG. 5C schematically illustrates the magnetic field 514 of the external magnet 530 of FIGS. 5A-5B in relation to at least one planar ferrite component 220 in accordance with certain embodiments described herein. The at least one planar ferrite component 220 of FIG. 5C is positioned above and parallel to the at least one external inductive communication coil 130 (not shown in FIG. 5C), the at least one external inductive communication coil 130 configured to be in inductive communication with at least one internal inductive communication coil 136 of the implanted device 600. The magnetic field 514 of the external magnet 530 extends to and substantially perpendicularly intersects the at least one planar ferrite component 220. In certain such embodiments, the external magnet 530 is configured to interact with the implanted device 600 to provide sufficient magnetic force to retain the assembly 500 over the implanted device 600 while providing the same advantage of not saturating the at least one planar ferrite component 220 (e.g., does not reduce the shielding provided by the at least one planar ferrite component 220 of the other components of the circuitry of the external transmitter unit 128 from the magnetic fields generated by the at least one external inductive communication coil 130; does not adversely affect, interfere with, degrade performance of the assembly 500) as does the axially magnetized magnet 210 of FIGS. 2A-2B.

The external magnet 530 of certain embodiments comprises four poles: two "north" poles (labeled "N") and two "south" poles (labeled "S"). FIGS. 5A-5B schematically illustrate the external magnet 530 comprises two half portions each having one "north" pole and one "south" pole (e.g., each half portion having a corresponding magnetization comprising a magnetic dipole moment, with substantially equal magnitudes and substantially opposite directions). In FIGS. 5A-5B, the external magnet 530 is bisected by the first width (e.g., first diameter) between the first half portion and the second half portion such that the first half portion is a semicircular first portion 531 and the second half portion is a semicircular second portion 533, with both the first and second magnetic dipole moments 532, 534 oriented substantially parallel to a center axis 535 of the external magnet 530. The external magnet 530 is mounted to the housing 510 such that first magnetic dipole moment 532 and the second magnetic dipole moment 534 of FIGS. 5A-5B are substantially perpendicular to the portion of skin 300 during operation of the circuitry 520.

Figure 6B:
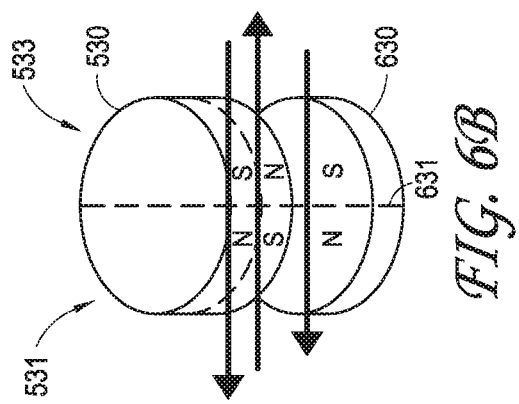
FIGS. 6A-6B schematically illustrate an alternative view of the external magnet of FIGS. 5A-5B in accordance with certain embodiments described herein.
Figure 6A:
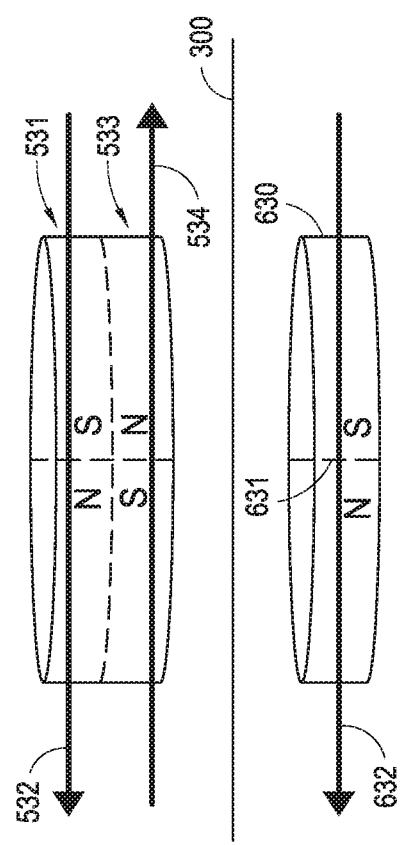

FIGS. 6A-6B schematically illustrate an alternative view of the external magnet 530 of FIGS. 5A-5B in accordance with certain embodiments described herein. As in FIGS. 5A-5B, the external magnet 530 comprises two portions each having one "north" pole and one "south" pole (e.g., each portion having a corresponding magnetization comprising a magnetic dipole moment, with substantially equal magnitudes and substantially opposite directions). However, in FIGS. 6A-6B, the first portion 531 has a right circular cylindrical shape having a second width (e.g., diameter) substantially equal to the first width (e.g., diameter) and the second portion 533 has a right circular cylindrical shape having a third width (e.g., diameter) substantially equal to the first width (e.g., diameter). In certain embodiments, as schematically illustrated by FIGS. 6A-6B, the first portion 531 has a second height substantially equal to one-half the first height, and the second portion 533 has a third height substantially equal to one-half the first height. In certain other embodiments, the second height is less than the third height. For example, the external magnet 530 of FIGS. 6A-6B can be a separable unitary member (e.g., in which the first portion 531 and the second portion 533 are configured to be repeatedly and reversibly separated from one another and repeatedly and reversibly rejoined to one another without damaging the magnet 530), with the first portion 531 having a smaller height than does the second portion 533. The external magnet 530 of FIGS. 6A-6B is configured to be mounted to the housing 510 such that the first magnetic dipole moment 532 and the second magnetic dipole moment 534 of FIGS. 6A-6B are substantially parallel to the portion of skin 300 during operation of the circuitry 520.

In certain embodiments, the internal magnet 630 is also a unitary (e.g., monolithic) magnet comprising a plurality of magnetized portions with different magnetizations from one another (e.g., at least one first magnetic dipole moment having a first magnitude and a first direction and at least one second magnetic dipole moment having a second magnitude substantially equal to the first magnitude and a second direction substantially opposite to the first direction). The at least one first magnetic dipole moment of the internal magnet 630 and the at least one second magnetic dipole moment of the internal magnet 630 can be configured to produce a magnetic field configured to, when the external apparatus 500 is placed over the portion of skin 300, attract the internal magnet 630 to the external apparatus 500 (e.g., to the external magnet 530). As described herein with regard to the external magnet 530, the internal magnet 630 of certain embodiments has a first width that is substantially parallel to the portion of skin 300 and a first height that is substantially perpendicular to the portion of skin upon implantation of the housing 610. The internal magnet 630 of certain embodiments comprises a first portion generating the first magnetic dipole moment and a second portion generating the second magnetic dipole moment. In certain embodiments, the first portion comprises a first half of the internal magnet 630 and the second portion comprises a second half of the internal magnet 630. For example, the first width can bisect the internal magnet 630 between the first half and the second half and the first direction and the second direction can be substantially perpendicular to the portion of skin 300 upon implantation of the housing 610. For another example, the first portion can have a second width substantially equal to the first width and a second height substantially equal to one-half the first height, and the second portion can have a third width substantially equal to the first width and a third height substantially equal to one-half the first height, and the first direction and the second direction can be substantially parallel to the portion of skin 300 upon implantation of the housing 610.

FIGS. 7A-7F schematically illustrate various example configurations of an external magnet 530 and an internal magnet 630 in accordance with certain embodiments described herein. In each of FIGS. 7A-7F, both the external magnet 530 and the internal magnet 630 is a multipole magnet (e.g., a magnet having two or more portions with different magnetizations). The magnetizations (e.g., magnetic dipole moments) of the various portions of the magnets are schematically shown by arrows. While the external magnet 530 and the internal magnet 630 of FIGS. 7A-7F are shown as having right circular cylindrical shapes, other shapes are also compatible with certain embodiments described herein.

In FIG. 7A, the external magnet 530 comprises two half portions 531, 533 (e.g., semicircular half portions) having magnetizations 532, 534 with substantially equal magnitudes and substantially opposite directions (e.g., substantially perpendicular to the portion of skin 300), and the internal magnet 630 comprises two half portions 633, 635 (e.g., semicircular half portions) having magnetizations 634, 636 with substantially equal magnitudes and substantially opposite directions (e.g., substantially perpendicular to the portion of skin 300).

In FIG. 7B, the external magnet 530 comprises first and second portions 531, 533 having magnetizations 532, 534 with substantially equal magnitudes and substantially opposite directions (e.g., substantially perpendicular to the portion of skin 300) and a third portion 537 between the first portion 531 and the second portion 533. The third portion 537 has a magnetization 538 that is substantially perpendicular to the magnetizations 532, 534 of the first portion 531 and the second portion 533. Similarly, the internal magnet 630 of FIG. 7B comprises first and second portions 633, 635 having magnetizations 634, 636 with substantially equal magnitudes and substantially opposite directions (e.g., substantially perpendicular to the portion of skin 300) and a third portion 637 between the first portion 633 and the second portion 635, the third portion 637 has a magnetization 638 that is substantially perpendicular to the magnetizations 634, 636 of the first portion 633 and the second portion 635. The magnetization 538 of the third portion 537 of the external magnet 530 is substantially equal and opposite to the magnetization 638 of the third portion 637 of the internal magnet 630.

In FIG. 7C, the external magnet 530 comprises first and second portions 531, 533 having magnetizations 532, 534 with substantially equal magnitudes and substantially opposite directions (e.g., substantially perpendicular to the portion of skin 300) and a third portion 537 between the first portion 531 and the second portion 533, the third portion 537 having a magnetization 538 that is substantially perpendicular to the magnetizations 532, 534 of the first portion 531 and the second portion 533. The internal magnet 630 comprises two half portions 633, 635 (e.g., semicircular half portions) having magnetizations 634, 636 with substantially equal magnitudes and substantially opposite directions (e.g., substantially perpendicular to the portion of skin 300).

In FIG. 7D, the external magnet 530 comprises a first portion 531 (e.g., a right circular cylindrical portion) and the second portion 533 surrounding a perimeter of the first portion 531 (e.g., a right circular cylindrical ring portion 533 concentric with the first portion 531). In certain embodiments, the magnetizations 532, 534 of the first and second portions 531, 533 of the external magnet 530 have substantially equal magnitudes and are in substantially opposite directions. Similarly, the internal magnet 630 comprises a first portion 633 (e.g., a right circular cylindrical portion) and a second portion 635 surrounding a perimeter of the first portion 633 (e.g., a right circular cylindrical ring portion 635 concentric with the first portion 633). In certain embodiments, the magnetizations 634, 636 of the first and second portions 633, 635 of the internal magnet 630 have substantially equal magnitudes and are in substantially opposite directions.

In FIG. 7E, the external magnet 530 comprises a first portion 531 (e.g., a right circular cylindrical portion) and a second portion 533 surrounding a perimeter of the first portion 531 (e.g., a right circular cylindrical ring portion 533 concentric with the first portion 531), the first and second portions 531, 533 having magnetizations substantially perpendicular to the portion of skin 300, and a third portion 537 between the first portion 531 and the second portion 533, the third portion 537 has a magnetization 538 that is substantially perpendicular to the magnetizations 532, 534 of the first portion 531 and the second portion 533. Similarly, the internal magnet 630 comprises a first portion 633 (e.g., a right circular cylindrical portion) and a second portion 635 surrounding a perimeter of the first portion 633 (e.g., a right circular cylindrical ring portion 635 concentric with the first portion 633), the first and second portions 633, 635 having magnetizations 634, 636 substantially perpendicular to the portion of skin 300, and a third portion 637 between the first portion 633 and the second portion 635, the third portion 637 having a magnetization 638 that is substantially perpendicular to the magnetizations 634, 636 of the first portion 633 and the second portion 635. In certain embodiments, the magnetizations 532, 534 of the first and second portions 531, 533 of the external magnet 530 are substantially equal and opposite to one another, the magnetizations 634, 636 of the first and second portions 633, 635 of the internal magnet 630 are substantially equal and opposite to one another, and the magnetization 538 of the third portion 537 of the external magnet 530 and the magnetization 638 of the third portion 637 of the internal magnet 630 are substantially equal and opposite to one another.

In FIG. 7F, the external magnet 530 comprises a first portion 531 (e.g., a right circular cylindrical portion) and a second portion 533 surrounding a perimeter of the first portion 531 (e.g., a right circular cylindrical ring portion 533 concentric with the first portion 531), the first and second portions 531, 533 having magnetizations 532, 534 substantially perpendicular to the portion of skin 300, and a third portion 537 between the first portion 531 and the second portion 533, the third portion 537 has a magnetization 538 that is substantially perpendicular to the magnetizations 532, 534 of the first portion 531 and the second portion 533. In certain embodiments, the magnetizations 532, 534 of the first and second portions 531, 533 of the external magnet 530 are substantially equal and opposite to one another. The internal magnet 630 comprises a first portion 633 (e.g., a right circular cylindrical portion) and a second portion 635 surrounding a perimeter of the first portion 633 (e.g., a right circular cylindrical ring portion 635 concentric with the first portion 633). In certain embodiments, the magnetizations 634, 636 of the first and second portions 633, 635 of the internal magnet 630 have substantially equal magnitudes and are in substantially opposite directions.

In certain embodiments, the external magnet 530 and/or the internal magnet 630 provides increased retention force (e.g., for the same magnet size and weight) for a range of thicknesses of the portion of skin 300 (e.g., the skin flap thickness) between the external apparatus 500 and the implanted device 600. Certain such embodiments advantageously provide a lighter external apparatus 500 and/or implanted device 600 for equivalent retention force. This effect is even more pronounced when both the external magnet 530 and the internal magnet 630 are multipole magnets.

Figure 8:
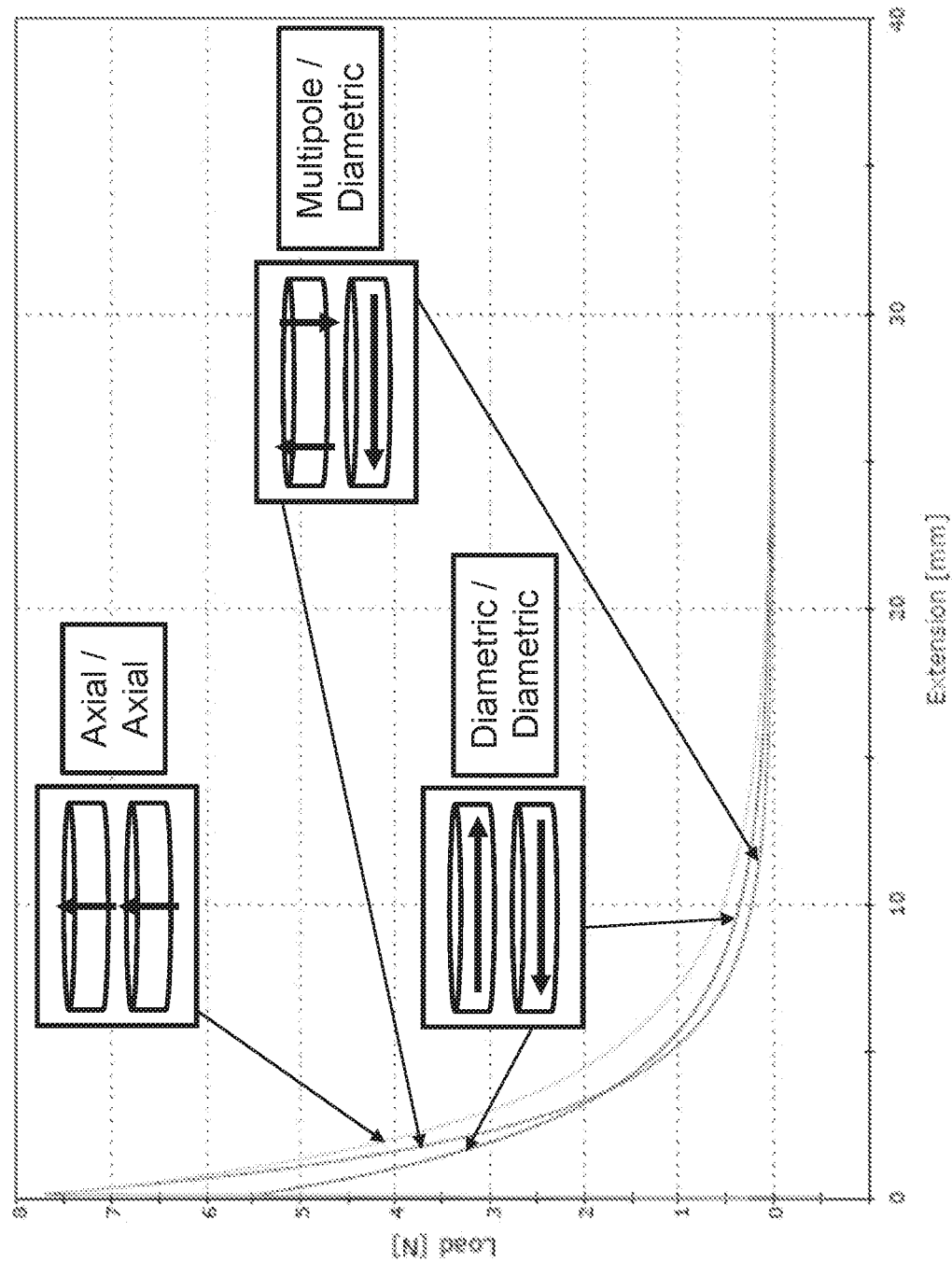
FIG. 8 is a plot that compares the retention force provided by three external/internal magnet configurations.

FIG. 8 is a plot that compares the retention force provided by three external/internal magnet configurations. Each of the magnets had a right circular cylindrical shape with a diameter of 12 millimeters and a height of 6 millimeters. A first configuration of an axially polarized external magnet and an axially polarized internal magnet exhibited the largest retention forces for all magnet separation distances. For smaller magnet separation distances (e.g., less than about 3-4 millimeters), a second configuration of a multipole external magnet in accordance with certain embodiments described herein and a diametrically magnetized internal magnet had larger retention forces than did a third configuration of a diametrically magnetized external magnet and a diametrically magnetized internal magnet. For larger magnet separation distances (e.g., greater than about 3-4 millimeters), the third configuration had larger retention forces than did the second configuration. Therefore, for small skin flap thicknesses (e.g., less than 4 millimeters), in certain embodiments, a smaller multipole external magnet can provide a retention force equivalent to that of a larger diametrically magnetized external magnet. Thus, in certain embodiments, the multipole external magnet in conjunction with a diametrically magnetized internal magnet can provide superior retention forces than does an equivalently-sized diametrically magnetized external magnet in conjunction with the same diametrically magnetized internal magnet while also providing desirable MRI compatibility.

It is to be appreciated that the embodiments disclosed herein are not mutually exclusive and may be combined with one another in various arrangements.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. An auditory prosthesis, comprising:
an external component including an external magnet; and
an internal component including an internal magnet, wherein
the external magnet is configured to interact with the internal magnet to provide sufficient magnetic force to retain the external component over the internal component,
the external magnet has two magnetic dipole moments,
the internal magnet has only two magnetic dipole moments,
the external component includes an inductor coil that encircles the external magnet and/or encircles a projection of the external magnet onto a plane defined by the inductor coil, and
at least one of:
(i) a first of the magnetic dipole moments of the two magnetic dipole moments of the external magnet departs from parallel with a center axis of the external magnet by more than 5 degrees and departs from perpendicular with the center axis of the external magnet by more than 5 degrees and a second of the magnetic dipole moments of the two magnetic dipole moments of the external magnet departs from parallel with the center axis of the external magnet by more than 5 degrees and departs from perpendicular with the center axis of the external magnet by more than 5 degrees;
the first and second magnetic dipole moments of the two magnetic dipole moments of the external magnet are oblique relative to one another;
the first of the magnetic dipole moments of the two magnetic dipole moments of the external magnet has an equal magnitude to that of the second of the magnetic dipole moments of the two magnetic dipole moments of the external magnet;
an axis of the first of the magnetic dipole moments of the two magnetic dipole moments of the external magnet mirrors an axis of the second of the magnetic dipole moments of the two magnetic dipole moments of the external magnet relative to a first plane coincident with the center axis of the external magnet; and
the axis of the first of the magnetic dipole moments of the two magnetic dipole moments of the external magnet lies on a second plane coincident with the center axis of the external magnet and the axis of the second of the magnetic dipole moments of the two magnetic dipole moments of the external magnet lies on the second plane coincident with the center axis of the external magnet; or
(ii) a first of the magnetic dipole moments of the only two magnetic dipole moments of the internal magnet departs from parallel with a center axis of the internal magnet by more than 5 degrees and departs from perpendicular with the center axis of the internal magnet by more than 5 degrees and a second of the magnetic dipole moments of the only two magnetic dipole moments of the internal magnet departs from parallel with the center axis of the internal magnet by more than 5 degrees and departs from perpendicular with the center axis of the internal magnet by more than 5 degrees;

the first and second magnetic dipole moments of the only two magnetic dipole moments of the internal magnet are oblique relative to one another;

the first of the magnetic dipole moments of the only two magnetic dipole moments of the internal magnet has an equal magnitude to that of the second of the magnetic dipole moments of the only two magnetic dipole moments of the internal magnet;

an axis of the first of the magnetic dipole moments of the only two magnetic dipole moments of the internal magnet mirrors an axis of the second of the magnetic dipole moments of the only two magnetic dipole moments of the internal magnet relative to a first plane coincident with the center axis of the internal magnet; and the axis of the first of the magnetic dipole moments of the only two magnetic dipole moments of the internal magnet lies on a second plane coincident with the center axis of the internal magnet and the axis of the second of the magnetic dipole moments of the only two magnetic dipole moments of the internal magnet lies on the second plane coincident with the center axis of the internal magnet.

2. The auditory prosthesis of claim 1, wherein the external magnet includes a third magnetic dipole moment, and the auditory prosthesis is configured so that the third magnetic dipole moment is at least substantially parallel to skin above the internal component.

3. The auditory prosthesis of claim 1, wherein the external magnet has only two magnetic dipole moments.

4. The auditory prosthesis of claim 1, wherein the external magnet includes only three magnetic dipole moments and a third of the only three magnetic dipole moments has a direction oblique to respective directions of the first and second magnetic dipole moments of the external magnet.

5. The auditory prosthesis of claim 1, wherein the auditory prosthesis is configured so that the first of the two magnetic dipole moments of the external magnet has a direction falling within plus or minus 10 degrees from perpendicular to skin below the external component when the external component is magnetically coupled to the internal component when the internal component is implanted in a recipient.

6. The auditory prosthesis of claim 5, wherein the auditory prosthesis is configured so that the second of the two magnetic dipole moments of the external magnet has a direction falling within plus or minus 10 degrees from perpendicular to skin below the external component when the external component is magnetically coupled to the internal component when the internal component is implanted in a recipient.

7. The auditory prosthesis of claim 1, wherein the auditory prosthesis is configured so that the first of the only two magnetic dipole moments of the internal magnet has a direction falling within plus or minus 10 degrees from perpendicular to skin above the internal magnet when the external component is magnetically coupled to the internal component when the internal component is implanted in a recipient.

8. The auditory prosthesis of claim 1, wherein the internal magnet comprises only two magnets.

9. The auditory prosthesis of claim 1, wherein the internal magnet is a separable unitary member.

10. The auditory prosthesis of claim 1, wherein the internal magnet is a non-separable unitary member.

11. The auditory prosthesis of claim 1, wherein:
the internal component includes a stimulator unit and/or a stimulator/receiver unit; and
the auditory prosthesis includes a microphone.

12. The auditory prosthesis of claim 1, wherein:
the auditory prosthesis includes a sound processor unit.

13. The auditory prosthesis of claim 1, wherein:
the internal magnet is a means for generating a permanent magnetic field.

14. The auditory prosthesis of claim 1, wherein:
the first of the magnetic dipole moments of the only two magnetic dipole moments of the internal magnet departs from parallel with the center axis of the internal magnet by more than 5 degrees and departs from perpendicular with the center axis of the internal magnetic by more than 5 degrees and the second of the magnetic dipole moments of the only two magnetic dipole moments of the internal magnet departs from parallel with the center axis of the internal magnet by more than 5 degrees and departs from perpendicular with the center axis of the internal magnet by more than 5 degrees;

the first and second magnetic dipole moments of the only two magnetic dipole moments of the internal magnet are oblique relative to one another;

the first of the magnetic dipole moments of the only two magnetic dipole moments of the internal magnet has an equal magnitude to that of the second of the magnetic dipole moments of the only two magnetic dipole moments of the internal magnet;

the axis of the first of the magnetic dipole moments of the only two magnetic dipole moments of the internal magnet mirrors an axis of the second of the magnetic dipole moments of the only two magnetic dipole moments of the internal magnet relative to the first plane coincident with the center axis of the internal magnet; and the axis of the first of the magnetic dipole moments of the only two magnetic dipole moments of the internal magnet lies on the second plane coincident with the center axis of the internal magnet and the axis of the second of the magnetic dipole moments of the internal magnet lies on the second plane coincident with the center axis of the internal magnet.

15. The auditory prosthesis of claim 14, wherein the internal magnet is disk shaped.

16. The auditory prosthesis of claim 1, wherein:
the first of the magnetic dipole moments of the two magnetic dipole moments of the external magnet is established by a distinct first magnet portion of the external magnet and the second of the magnetic dipole moments of the two magnetic dipole moments of the external magnet is established by a distinct second magnet portion of the external magnet; and the first of the magnetic dipole moments of the only two magnetic dipole moments of the internal magnet is established by a distinct first magnet portion of the internal magnet and the second of the magnetic dipole moments of the only two magnetic dipole moments of the internal magnet is established by a distinct second magnet portion of the internal magnet.

17. The auditory prosthesis of claim 1, wherein:
the first of the magnetic dipole moments of the two magnetic dipole moments of the external magnet and the second of the magnetic dipole moments of the two magnetic dipole moments of the external magnet are established by a single portion of the external magnet; and the first of the magnetic dipole moments of the only two magnetic dipole moments of the internal magnet and the second of the magnetic dipole moments of the only two magnetic dipole moments of the internal magnet are established by a single portion of the internal magnet.

18. An auditory prosthesis, comprising:
an external component including an external magnet; and
an internal component including an internal magnet, wherein
the external magnet is configured to interact with the internal magnet to provide sufficient magnetic force to retain the external component over the internal component,
the internal magnet comprises two portions having separate magnetic dipole moments, the two portions including a first portion that includes a first half of the internal magnet and a second portion that includes the second half of the internal magnet,
a first of the separate magnetic dipole moments departs from parallel with a center axis of the internal magnet by more than 5 degrees and departs from perpendicular with the center axis by more than 5 degrees and a second of the separate magnetic dipole moments departs from parallel with the center axis of the internal magnet by more than 5 degrees and departs from perpendicular with the center axis of the internal magnet by more than 5 degrees;
the first and second of the separate magnetic dipole moments of the two magnetic dipole moments of the internal magnet are oblique relative to one another;
the first of the separate magnetic dipole moments has an equal magnitude to that of the second of the separate magnetic dipole moments;
an axis of the first of the separate magnetic dipole moments mirrors an axis of the second of the separate magnetic dipole moments relative to a first plane coincident with the center axis of the internal magnet; and
the axis of the first of the separate magnetic dipole moments lies on a second plane coincident with the center axis and the axis of the second of the separate magnetic dipole moments lies on the second plane coincident with the center axis.

19. The auditory prosthesis of claim 18, wherein the internal magnet is a non-separable unitary member.

20. The auditory prosthesis of claim 18, wherein the internal magnet is a separable unitary member.

21. The auditory prosthesis of claim 18, wherein the first portion can be separated from the second portion when the internal magnet is not mounted on or within a housing.

22. The auditory prosthesis of claim 21, wherein the two portions can be joined or rejoined together prior to being placed in mechanical communication with other portions of the internal component.

23. The auditory prosthesis of claim 18, wherein the two portions are configured to be repeatedly and reversibly separated from one another and repeatedly and reversibly rejoined to one another without damaging the internal magnet.

24. The auditory prosthesis of claim 18, wherein the internal magnet is disk shaped.

25. The auditory prosthesis of claim 18, wherein the external magnet has only one diametrically magnetized portion.

26. The auditory prosthesis of claim 25, wherein the auditory prosthesis is configured so that the diametrically magnetized portion has a magnetic dipole moment with a direction parallel to skin plus or minus 10 degrees when the external component is magnetically coupled to the internal component when the internal component is implanted in a recipient.

27. The auditory prosthesis of claim 26, wherein the diametrically magnetized portion is part of a compilation that further includes two magnet portions that have magnetic dipoles that extend at a non-zero angle more than 5 degrees relative to a magnetic dipole of the diametrically magnetized portion.

28. The auditory prosthesis of claim 25, wherein the diametrically magnetized portion has a magnetic dipole moment with a direction parallel to skin plus or minus 10 degrees.

29. The auditory prosthesis of claim 28, wherein the diametrically magnetized portion is part of a compilation that further includes two magnet portions that have magnetic dipoles that extend at an angle more than 5 degrees relative to a magnetic dipole of the diametrically magnetized portion.

30. The auditory prosthesis of claim 18, wherein:
the external component includes an inductor coil that encircles the external magnet and/or encircles a projection of the external magnet onto a plane defined by the inductor coil.

31. The auditory prosthesis of claim 18, wherein:
the auditory prosthesis includes a sound processor unit and a microphone.

32. The auditory prosthesis of claim 18, wherein:
the internal component includes an elongate electrode assembly; and
the external component includes an external transmitter unit.

33. The auditory prosthesis of claim 18, wherein the first of the separate magnetic dipole moments extends away from a surface of the internal magnet facing toward the external magnet at a first non-orthogonal angular direction, wherein the second of the separate magnetic dipole moments extends away from a surface of the internal magnet facing away from the external magnet at a second non-orthogonal angular direction.

34. The auditory prosthesis of claim 18, wherein the first of the separate magnetic dipole moments departs from parallel with the center axis of the internal magnet by at least 10 degrees and departs from perpendicular with the center axis of the internal magnet by at least 10 degrees and the second of the separate magnetic dipole moments departs from parallel with the center axis of the internal magnet by at least 10 degrees and departs from perpendicular with the center axis by at least 10 degrees.

35. The auditory prosthesis of claim 18, wherein:
the internal magnet comprises a unitary member with the two portions having separate magnetic dipoles.

36. The auditory prosthesis of claim 18, wherein:
the internal magnet is a monolithic member with the two portions having separate magnetic dipoles.

37. The auditory prosthesis of claim 18, wherein:
the internal magnet is a non-monolithic magnet.

38. The auditory prosthesis of claim 18, wherein:
the internal magnet is such that the two portions comprise respectively a first magnet and a second magnet separate from the first magnet.

39. The auditory prosthesis of claim 18, wherein:
the internal magnet is a non-monolithic apparatus made up by the two portions.

40. An auditory prosthesis, comprising:
an external component including an external magnet; and
an internal component including an internal magnet, wherein
the external magnet is configured to interact with the internal magnet to provide sufficient magnetic force to retain the external component over the internal component, and
at least one of:
(i) the external magnet comprises two magnetic dipole moments that depart from parallel and from perpendicular to a center axis of the external magnet, wherein a first of the magnetic dipole moments of the two magnetic dipole moments of the external magnet departs from parallel with the center axis of the external magnet by more than 5 degrees and departs from perpendicular with the center axis of the external magnet by more than 5 degrees and a second of the magnetic dipole moments of the two magnetic dipole moments of the external magnet departs from parallel with the center axis of the external magnet by more than 5 degrees and departs from perpendicular with the center axis of the external magnet by more than 5 degrees;
the first and second magnetic dipole moments of the two magnetic dipole moments of the external magnet are oblique relative to one another;
the first of the magnetic dipole moments of the two magnetic dipole moments of the external magnet has an equal magnitude to that of the second of the magnetic dipole moments of the two magnetic dipole moments of the external magnet;
an axis of the first of the magnetic dipole moments of the two magnetic dipole moments of the external magnet mirrors an axis of the second of the magnetic dipole moments of the two magnetic dipole moments of the external magnet relative to a first plane coincident with the center axis of the external magnet; and
the axis of the first of the magnetic dipole moments of the two magnetic dipole moments of the external magnet lies on a second plane coincident with the center axis of the external magnet and the axis of the second of the magnetic dipole moments of the two magnetic dipole moments of the external magnet lies on the second plane coincident with the center axis of the external magnet; or
(ii) the internal magnet comprises two magnetic dipole moments that depart from parallel and from perpendicular to a center axis of the internal magnet, wherein a first of the magnetic dipole moments of two magnetic dipole moments of the internal magnet departs from parallel with the center axis of the internal magnet by more than 5 degrees and departs from perpendicular with the center axis of the internal magnet by more than 5 degrees and a second of the magnetic dipole moments of the two dipole moments of the internal magnet departs from parallel with the center axis of the internal magnet by more than 5 degrees and departs from perpendicular with the center axis of the internal magnet by more than 5 degrees;
the first and second magnetic dipole moments of the two magnetic dipole moments of the internal magnet are oblique relative to one another;
the first of the magnetic dipole moments of the two magnetic dipole moments of the internal magnet has an equal magnitude to that of the second of the magnetic dipole moments of the two magnetic dipole moments of the internal magnet;
an axis of the first of the magnetic dipole moments of the two magnetic dipole moments of the internal magnet always mirrors an axis of the second of the magnetic dipole moments of the two magnetic dipole moments of the internal magnet relative to a first plane coincident with the center axis of the internal magnet; and
the axis of the first of the magnetic dipole moments of the two magnetic dipole moments of the internal magnet lies on a second plane coincident with the center axis of the internal magnet and the axis of the second of the magnetic dipole moments of the internal magnet lies on the second plane coincident with the center axis of the internal magnet.

41. The auditory prosthesis of claim 40, wherein the two magnetic dipole moments of the internal magnet depart from parallel with the center axis by 10 degrees.

42. The auditory prosthesis of claim 40, wherein the two magnetic dipole moments of the internal magnet depart from perpendicular with the center axis by 10 degrees.

43. The auditory prosthesis of claim 40, wherein the external magnet is a unitary member and is a non-separable unitary member and/or the internal magnet is a unitary member and is a non-separable unitary member.

44. The auditory prosthesis of claim 40, wherein the external magnet is a unitary member that is a separable unitary member and/or the internal magnet is a unitary member that is a separable unitary member.

45. The auditory prosthesis of claim 40, wherein the external magnet comprises:
the two magnetic dipole moments that depart from parallel and from perpendicular to the center axis of the external magnet, wherein the first of the magnetic dipole moments of the two magnetic dipole moments of the external magnet departs from parallel with the center axis of the external magnet by more than 5 degrees and departs from perpendicular with the center axis of the external magnet by more than 5 degrees and the second of the magnetic dipole moments of the two magnetic dipole moments of the external magnet departs from parallel with the center axis of the external magnet by more than 5 degrees and departs from perpendicular with the center axis of the external magnet by more than 5 degrees, wherein
the first and second magnetic dipole moments of the two magnetic dipole moments of the external magnet are oblique relative to one another,
the first of the magnetic dipole moments of the two magnetic dipole moments of the external magnet has the equal magnitude to that of the second of the magnetic dipole moments of the two magnetic dipole moments of the external magnet,
the axis of the first of the magnetic dipole moments of the two magnetic dipole moments of the external magnet mirrors the axis of the second of the magnetic dipole moments of the two magnetic dipole moments of the external magnet relative to the first plane coincident with the center axis of the external magnet, and the axis of the first of the magnetic dipole moments of the two magnetic dipole moments of the external magnet lies on the second plane coincident with the center axis of the external magnet and the axis of the second of the magnetic dipole moments of the two magnetic dipole moments of the external magnet lies on the second plane coincident with the center axis of the external magnet.

46. The auditory prosthesis of claim 40, wherein the internal magnet comprises:

the two magnetic dipole moments that depart from parallel and from perpendicular to a center axis of the internal magnet, wherein the first of the magnetic dipole moments of two magnetic dipole moments of the internal magnet departs from parallel with the center axis of the internal magnet by more than 5 degrees and departs from perpendicular with the center axis of the internal magnet by more than 5 degrees and the second of the magnetic dipole moments of the two dipole moments of the internal magnet departs from parallel with the center axis of the internal magnet by more than 5 degrees and departs from perpendicular with the center axis of the internal magnet by more than 5 degrees, wherein the first and second magnetic dipole moments of the two magnetic dipole moments of the internal magnet are oblique relative to one another, the first of the magnetic dipole moments of the two magnetic dipole moments of the internal magnet has the equal magnitude to that of the second of the magnetic dipole moments of the two magnetic dipole moments of the internal magnet, the axis of the first of the magnetic dipole moments of the two magnetic dipole moments of the internal magnet always mirrors the axis of the second of the magnetic dipole moments of the two magnetic dipole moments of the internal magnet relative to the first plane coincident with the center axis of the internal magnet, and the axis of the first of the magnetic dipole moments of the two magnetic dipole moments of the internal magnet lies on the second plane coincident with the center axis of the internal magnet and the axis of the second of the magnet dipole moments of the two magnetic dipole moments of the internal magnet lies on the second plane coincident with the center axis of the internal magnet.

47. The auditory prosthesis of claim 40, wherein the external component includes an inductor coil that encircles the external magnet and/or encircles a projection of the external magnet onto a plane defined by the inductor coil.

48. The auditory prosthesis of claim 40, wherein the two magnetic dipole moments of the internal magnet depart from parallel with the center axis by at least 10 degrees and depart from perpendicular with the center axis by at least 10 degrees.

49. The auditory prosthesis of claim 40, wherein:

the internal magnet is a means for generating a permanent magnetic field.

50. The auditory prosthesis of claim 40, wherein the external magnet comprises two separate magnet portions respectively establishing the two magnetic dipole moments of the external magnet.

51. The auditory prosthesis of claim 40, wherein the external magnet comprises three separate magnet portions respectively establishing the two magnetic dipole moments of the external magnet and a third magnetic dipole moment of the external magnet.

52. The auditory prosthesis of claim 40, wherein the internal magnet comprises two separate magnet portions respectively establishing the two magnetic dipole moments of the internal magnet.

53. The auditory prosthesis of claim 40, wherein the internal magnet has only two magnetic dipole moments and the external magnet has only three magnetic dipole moments.

54. The auditory prosthesis of claim 40, wherein:

the auditory prosthesis includes a sound processor unit and a microphone.

* * * * *